US006960469B2

(12) United States Patent
Leroy et al.

(10) Patent No.: US 6,960,469 B2
(45) Date of Patent: Nov. 1, 2005

(54) ADENOVIRAL VECTORS ENCODING AN ANTIBODY FUSED TO A CD4 EXTRACELLULAR DOMAIN

(75) Inventors: Pierre Leroy, Ernolsheim-lès-Saverne (FR); Majid Mehtali, Plobsheim (FR)

(73) Assignee: Transgene S.A., Strasbourg Cedex (FR)

( * ) Notice: Subject to any disclaimer, the term of this patent is extended or adjusted under 35 U.S.C. 154(b) by 0 days.

(21) Appl. No.: 09/927,933

(22) Filed: Aug. 13, 2001

(65) Prior Publication Data

US 2002/0107869 A1 Aug. 8, 2002

Related U.S. Application Data

(62) Division of application No. 08/809,110, filed as application No. PCT/FR95/01171 on Sep. 13, 1995.

(30) Foreign Application Priority Data

Sep. 13, 1994 (FR) .............................. 94 10911

(51) Int. Cl.[7] ...................... C12N 15/861; C12N 15/13; C12N 15/62; A61K 48/00
(52) U.S. Cl. .................... 435/320.1; 435/325; 435/455; 435/456; 424/93.2; 424/93.21; 536/23.4; 536/23.53
(58) Field of Search ............................. 435/320.1, 455, 435/456, 325; 424/93.2, 93.21; 536/23.4, 23.53

(56) References Cited

U.S. PATENT DOCUMENTS

| 5,219,740 | A | | 6/1993 | Miller et al. ................ 435/69.1 |
| 5,314,995 | A | * | 5/1994 | Fell, Jr. et al. ............. 530/351 |
| 6,159,947 | A | | 12/2000 | Schweighoffer et al. |
| 6,294,377 | B1 | * | 9/2001 | Haddada et al. .......... 435/320.1 |

FOREIGN PATENT DOCUMENTS

| FR | 2706486 | 12/1994 |
| WO | 90/01550 | 2/1990 |
| WO | 92/15676 | 9/1992 |
| WO | 93/03143 | 2/1993 |
| WO | 94/06920 | 3/1994 |
| WO | 94/10323 | 5/1994 |
| WO | 94/19017 | 9/1994 |

OTHER PUBLICATIONS

Berkner, K.L. "Expression of heterologous sequences in adenoviral vectors," Curr. Top. Microbiol. Immunol. 158: 39–66, 1992.*
Berkner, K.L., "Expression of heterologous sequences in adenoviral vectors," Curr. Top. Microbiol. Immunol. 158:39–66, 1992.*

Kolls et al., "Prolonged and effective blockade of tumor necrosis factor activity through adenovirus–mediated gene transfer," Proc. Natl. Acad. Sci. USA 91: 215–219, Jan. 1994.*
Chen et al., "Intracellular Antibodies as a New Class of Therapeutic Molecules for Gene Therapy", Human Gene Therapy, (1994), vol. 5, No. 5, pp. 595–601, New York, NY, Mary Ann Liebert Inc., Los Angeles, USA.
D. Moritz et al, "Cytotoxic T Lymphocytes With a Grated Recognition Specificity for ERBB2–Expressing Tumor Cells", Proceedings of the National Academy of Science of the USA, May 1994, pp. 4318–4322, vol. 91, No. 10, 10 Washington, D.C., USA.
A. Conley et al., "Neutralization of Divergent Human Immunodeficiency Virus Type 1 Variants and Primary Isolates by IAM–41–2F5, an Anti–gp41 Human Monoclonal Antibody", Proceedings of the National Academy of Sciences, Apr. 1994, pp. 3348–3352, vol. 91, No. 8, 12 Washington D.C..
M. Rosenfeld et al., "E1–E3 Replication Deficient Recombinant Adenovirus Vector Containing the Human Cystic Fibrosis Transmembrane Conductance Regulator (CFTR) cDNA Does Not Replicate in Human Respiratory Epithelial Cells" Journal of Cellular Biochemistry, Supplement, Apr. 1993, p. 251, No. 17, Part E, 29–25 New York, NY, USA.
Crystal, R.G., Science, vol. 270, pp. 404–410, (1995), AAAS, Washington D.C., USA.
Orkin et al. NIH Report on the Investment in Research on Gene Therapy, (Dec. 1995), NIH, USA.
Verma et al., Nature, vol. 389, pp. 239–242, (Sep. 1997), MacMillin, London.
Anderson, W.F., Nature, vol. 392, Suppl. pp. 25–30, (Apr. 1998).
Brinkmann et al., Proc. Natl. Acad. Sci., U.S.A., vol. 88, pp. 8616–8620, (Oct. 1991).
Batra et al., Molecular and Cellular Biology, vol. 11(4): pp. 2200–2205.
Chaudhary et al. Proc. Natl. Acad. Sci., U.S.A., vol. 87, pp. 9491–9494, (Dec. 1990).
Marshall, E.M., Science, vol. 269, pp. 1050–1055, (Aug. 1995).

* cited by examiner

*Primary Examiner*—Scott D. Priebe
(74) *Attorney, Agent, or Firm*—Burns, Doane, Swecker & Mathis, LLP

(57) ABSTRACT

Genetically modified cell implant comprising an exogenous nucleotide sequence coding for all or part of an antibody, method for the preparation of such an implant and its therapeutic use for the treatment or prevention of an acquired disease. The invention also concerns an adenoviral vector, a pharmaceutical composition and its therapeutic use.

10 Claims, 11 Drawing Sheets

SEQUENCE LISTING

<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide OTG5168

<400> SEQUENCE: 1
ggaagcttcc atggacatga gggtc                25

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotide OTG5169

<400> SEQUENCE: 2
aagaattcct aacactctcc cctgt                25

<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide OTG5170

<400> SEQUENCE: 3
aaaagcttcc atggagttgg gtctg                    25

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide OTG5171

<400> SEQUENCE: 4
gggaattctc atttagccgg agaca                    25

<210> SEQ ID NO 5
<211> LENGTH: 27
<212> TYPE: DNA
<213> ORGANISM: Artificial Sequence
<220> FEATURE:
<223> OTHER INFORMATION: synthetic oligonucleotide OTG6114

<400> SEQUENCE: 5
gggaattcca ccatgggcat caagatg                  27

<210> SEQ ID NO 6
<211> LENGTH: 30
<212> TYPE: DNA
<213> ORGANISM: Artificial Sequence
<220> FEATURE:
<223> OTHER INFORMATION: synthetic oligonucleotide OTG6115

<400> SEQUENCE: 6
ggtctagatc taacactcat tcctgttgaa               30

<210> SEQ ID NO 7
<211> LENGTH: 27
<212> TYPE: DNA
<213> ORGANISM: Artificial Sequence
<220> FEATURE:
<223> OTHER INFORMATION: synthetic oligonucleotide OTG6192

<400> SEQUENCE: 7
ctgtcgacca ccatggatgg agcagag                  27

<210> SEQ ID NO 8
<211> LENGTH: 43
<212> TYPE: DNA
<213> ORGANISM: Artificial Sequence
<220> FEATURE:
<223> OTHER INFORMATION: synthetic oligonucleotide OTG6194

<400> SEQUENCE: 8
acgaattcgc ggccgcgctc cctccgccac ctttacccgg agt    43

<210> SEQ ID NO 9
<211> LENGTH: 26
<212> TYPE: DNA
<213> ORGANISM: Artificial Sequence
<220> FEATURE:
<223> OTHER INFORMATION: synthetic oligonucleotide OTG5147

-continued

```
<400> SEQUENCE: 9
ctgtggcggc cgccgcacag gttatc                                         26

<210> SEQ ID NO 10
<211> LENGTH: 28
<212> TYPE: DNA
<213> ORGANISM: Artificial Sequence
<220> FEATURE:
<223> OTHER INFORMATION: synthetic oligonucleotide OTG5148

<400> SEQUENCE: 10
caggcggccg cttttttcgt tatctgat                                       28

<210> SEQ ID NO 11
<211> LENGTH: 21
<212> TYPE: DNA
<213> ORGANISM: Artificial Sequence
<220> FEATURE:
<223> OTHER INFORMATION: synthetic oligonucleotide OTG5299

<400> SEQUENCE: 11
tacattacag cctcagaagc a                                              21

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide OTG6193

<400> SEQUENCE: 12
acgaattctc atttacccgg agt                                            23

<210> SEQ ID NO 13
<211> LENGTH: 35
<212> TYPE: DNA
<213> ORGANISM: Artificial Sequence
<220> FEATURE:
<223> OTHER INFORMATION: human CD4 cDNA

<400> SEQUENCE: 13
ccgctcgagc caccatgaac cggggagtcc cttttt                              35

<210> SEQ ID NO 14
<211> LENGTH: 30
<212> TYPE: DNA
<213> ORGANISM: Artificial Sequence
<220> FEATURE:
<223> OTHER INFORMATION: human CD4 cDNA

<400> SEQUENCE: 14
acaagatttg ggctcctgga aagctagcac                                     30

<210> SEQ ID NO 15
<211> LENGTH: 30
<212> TYPE: DNA
<213> ORGANISM: Artificial Sequence
<220> FEATURE:
<223> OTHER INFORMATION: cDNA of heavy chain of antibody 2F5

<400> SEQUENCE: 15
gtgctagctt tccaggagcc caaatcttgt                                     30

<210> SEQ ID NO 16
<211> LENGTH: 36
```

```
<212> TYPE: DNA
<213> ORGANISM: Artificial Sequence
<220> FEATURE:
<223> OTHER INFORMATION: cDNA of heavy chain of antibody 2F5

<400> SEQUENCE: 16
tgggcccggg atggggggcag ggtgtacacc tgtggt                              36

<210> SEQ ID NO 17
<211> LENGTH: 27
<212> TYPE: DNA
<213> ORGANISM: Artificial Sequence
<220> FEATURE:
<223> OTHER INFORMATION: human angiogenin cDNA

<400> SEQUENCE: 17
gggggatccc aggataactc caggtac                                         27

<210> SEQ ID NO 18
<211> LENGTH: 27
<212> TYPE: DNA
<213> ORGANISM: Artificial Sequence
<220> FEATURE:
<223> OTHER INFORMATION: human angiogenin cDNA

<400> SEQUENCE: 18
ggggaattct tacggacgac ggaaaat                                         27

<210> SEQ ID NO 19
<211> LENGTH: 30
<212> TYPE: DNA
<213> ORGANISM: Artificial Sequence
<220> FEATURE:
<223> OTHER INFORMATION: cDNA of heavy chain of antibody 2F5

<400> SEQUENCE: 19
tgcccccatc ccgggaggag atgaccaaga                                      30

<210> SEQ ID NO 20
<211> LENGTH: 36
<212> TYPE: DNA
<213> ORGANISM: Artificial Sequence
<220> FEATURE:
<223> OTHER INFORMATION: cDNA of heavy chain of antibody 2F5

<400> SEQUENCE: 20 ggggatccc ccgccaccett tagccggaga caggga                               36

<210> SEQ ID NO 21
<211> LENGTH: 7
<212> TYPE: PRT
<213> ORGANISM: Artificial Sequence
<220> FEATURE:
<223> OTHER INFORMATION: HIV gp41 2F5 epitope

<400> SEQUENCE: 21

Glu Leu Asp Lys Trp Ala Ser
1               5

<210> SEQ ID NO 22
<211> LENGTH: 5
<212> TYPE: PRT
<213> ORGANISM: Artificial Sequence
```

```
-continued

<220> FEATURE:
<223> OTHER INFORMATION: Linker

<400> SEQUENCE: 22

Gly Gly Gly Gly Ser
1               5
```

ADENOVIRAL VECTORS ENCODING AN ANTIBODY FUSED TO A CD4 EXTRACELLULAR DOMAIN

This application is a divisional of U.S. application Ser. No. 08/809,110, filed on Mar. 31, 1997, now abandoned, which was a national stage filing under 35 U.S.C. § 371 of International Application No. PCT/FR95/01171 filed on Sep. 13, 1995, which International Application was not published by the International Bureau in English on Mar. 21, 1996.

The present invention relates to a novel type of implant and its use for the treatment and prevention of cancer or of AIDS. More particularly, its subject is an implant comprising genetically modified cells capable of expressing and of secreting specific antibodies recognizing cancer cells or infected cells so as to inhibit at least partially their division or propagation as well as the production of viral particles in the infected cells. The present invention also relates to an adenoviral vector capable of directing the expression of a multimeric protein of interest as well as an antibody or one of its derivatives.

The possibility of treatments of human diseases by gene therapy has gone within a few years from the theoretical considerations stage to that of clinical applications. The first procedure applied to man was thus initiated in the United States in September 1990 on a genetically immunodeficient patient because of a mutation affecting the gene encoding Adenine Deaminase (ADA). The relative success of this first experimentation encouraged the development of new gene therapy procedures for various genetic or acquired diseases. Those currently under experimentation consist, for the most part, in transferring ex vivo the therapeutic gene into the patient's cells, for example the stem cells of the hematopoietic line, and then reinfusing these corrected cells into the patient. It is therefore a nonreversible, cumbersome technology which carries the risk of reimplanting transformed cells.

More recently initiated, the neo-organ technology makes it possible to overcome the major disadvantages of the conventional gene therapy procedures. It is based on the reimplantation, in the patient, of an artificial structure which may be called "implant" and comprising living cells, which are real "micro-factories" which make it possible to deliver the therapeutic molecule of interest in vivo and continuously.

More precisely, this artificial structure consists of living cells previously transduced by a viral vector carrying the therapeutic gene, which are included in a collagen gel coating a backbone of synthetic fibers of a biocompatible material (PTFE, polytetrafluoroethylene or Gore-Tex™). This gel also contains an angiogenic growth factor (bFGF, basic Fibroblast Growth Factor). After its reimplantation in the animal, the neo-organ is generally vascularized within a few days by virtue of the angiogenic and trophic properties of bFGF. It then develops into an autonomous structure, provided with a connective, sometimes innerated, tissue and linked to the bloodstream into which the therapeutic molecules are poured.

The possibility of using neo-organs for gene therapy has already been raised in several scientific articles as well as in international application WO 92/15676. However, the technology disclosed in the prior art documents deals with only the treatment of monogenic genetic diseases resulting from the defective and innate expression of a single gene, and has consequently been used only for the secretion of monomeric therapeutic molecules such as factor IX, $\alpha_1$-antitrypsin, ADA, erythropoietin (EPO) and $\beta$-glucuronidase. Up until now, this technology has not been suited to the secretion of more complex therapeutic molecules such as antibodies.

It has now been found that an implant of fibroblasts, genetically modified by a retroviral vector for the expression of the heavy and light chains of an anti-HIV antibody, once reimplanted in a mouse, is capable of continuously secreting into the bloodstream a large quantity of functional antibodies recognizing the infected cells carrying, at their surface, the antigen against which it is directed. The present invention is based on the fact that a fibroblast is capable of producing roughly stoichiometric quantities of heavy and light chains of an antibody capable of then associating into a tetramer to form a functional molecule. It offers the possibility of treating, by immunotherapy, acquired diseases and especially AIDS and cancer, two diseases whose complexity, seriousness as well as the absence of really satisfactory treatments, justify the development of novel technologies, such as that which is the subject of the present invention.

The present invention also provides adenoviral vectors capable of directing the expression of multimeric molecules of interest as well as of antibodies and derivatives thereof. They can be used to produce an immunotoxin directed against the HIV virus and to induce the selective destruction of infected cells.

Accordingly, the subject of the present invention is:
(1) an implant of genetically modified cells comprising an exogenous nucleotide sequence encoding all or part of an antibody, the said exogenous nucleotide sequence being placed under the control of the elements necessary for its expression and for the secretion of the said antibody, and
(2) a recombinant adenoviral vector comprising an exogenous nucleotide sequence encoding all or part of one or more protein(s) of interest capable of forming a multimer in a host cell; the said exogenous nucleotide sequence being placed under the control of the elements necessary for its expression in the said host cell.

For the purposes of the present invention, an implant designates any set of genetically modified living cells, as defined below and intended to be implanted in the human or animal body. Most particularly preferred is the case where the cells are attached to an extracelluar matrix, the whole forming a biocompatible and vascularizable structure. The matrix is preferably composed of collagen. However, other materials may be used within the framework of the present invention as long as they are biocompatible. It comprises especially (1) a biocompatible support such as synthetic fibers PTFE (polytetrafluoroethylene or Gore-Tex) coated with a collagen film so as to allow cell adhesion (2), a collagen gel in which the cells inside the implant are included and (3) an angiogenic agent promoting vascularization in the host. The term implant is a generic term which includes especially neo-organs and organoids.

Moreover, this may also involve encapsulated implants, that is to say included in a membrane of controlled porosity preventing especially the passage of cells (cells of the implant and cells of the host's immune system) but allowing the diffusion of the therapeutic molecule, nutrients and waste.

The term "genetically modified cell" refers to a cell having incorporated exogenous genetic material. The latter may be inserted into the genome of the cell or be present in episome form either in the cytoplasm or in the cell nucleus. The technology for introducing an exogenous genetic material into a cell is conventional and accessible to persons skilled in the art. In this regard, numerous vectors have been developed and are widely described in basic molecular biology manuals accessible to persons skilled in the art.

The genetically modified cells in use within the framework of the present invention comprise especially an exogenous nucleotide sequence. The latter may be a natural sequence (already present in the genome of the host cell) or a heterologous sequence, but it will have been introduced into the host cells by genetic engineering techniques (and therefore exogenously). Most particularly preferred is a sequence encoding a product which is not normally expressed therein or, if it is, at physiologically low concentrations. In accordance with the aims pursued by the present invention, the exogenous nucleotide sequence encodes all or part of an antibody. An antibody is a protein (immunoglobulin) normally produced by the B lymphocytes and which recognizes a specific foreign antigen and triggers the immune response. A native antibody is a tetramer composed of four protein chains: two light (L) chains and two heavy (H for heavy) chains associated with each other via disulfide bridges. The light chain consists of a variable region ($V_L$) at the N-terminal position and a constant region ($C_L$) at the C-terminal position whereas the heavy chain comprises from the N to the C-terminal a variable region ($V_H$) followed by three constant regions ($C_{H1}$, $C_{H2}$ and $C_{H3}$). The corresponding regions of the light and heavy chains associate to form distinct domains. The variable domain, formed by the association of the variable regions of the light and heavy chains of an immunoglobulin, is responsible for recognizing the corresponding antigen. The constant domains exert effector functions involved in the progress of the immune response.

For the purposes of the present invention, the two heavy and light chains may be identical (native antibodies). In this context, an exogenous nucleotide sequence is used which encodes a heavy chain and a light chain which will associate into a tetramer after their synthesis. However, a sequence may also be used which encodes only part of an antibody so as to produce, preferably, a fragment Fab (ab for antigen binding) or F(ab')$_2$, Fc (c for crystallizable) or scFv (sc for single chain and v for variable). Such fragments are described in detail in immunology manuals such as Immunology (third edition, 1993, Roitt, Brostoff and Male, ed Gambli, Mosby) and are schematically represented in FIG. 1. As regards more specifically the scFv fragment, it may be obtained from a sequence encoding a $V_L$ region followed by a $V_H$ region with optionally a spacer (of 1 to 10 neutral amino acid residues which are not very bulky) between the $V_L$ and $V_H$ sequences.

It is also possible to generate a chimeric (or hybrid) antibody derived from the fusion of sequences of diverse origins (species or types of antibody). In particular, it is possible to include or exchange constant regions derived from antibodies of different isotopes so as to confer new properties on the chimeric antibody, for example an enhancement of the cytotoxic reaction. This may also be a humanized antibody combining at least part of the variable regions of a mouse antibody and the constant regions of a human antibody. It is also possible to fuse one or more variable and/or constant regions or region parts of any origin, for example derived from light/or heavy chains in the form of a single-chain molecule.

Finally, another approach consists in producing a bispecific antibody comprising two variable domains, for example a domain recognizing an antigen carried by an infected or a tumor cell and the other a structure for activation of the immune response. This makes it possible to increase the activity of the killer cells in contact with the tumor or with the infected cell.

It goes without saying that an antibody in use in the present invention may have a sequence which is slightly different from the native sequence of an antibody. In practice, the common criterion for characterizing an antibody is its function, that is to say its capacity to bind specifically to the antigen against which it is directed. Numerous techniques which appear in general immunology manuals make it possible to demonstrate an antibody function, for example the ELISA, Western or fluorescence techniques. The invention extends to an antibody whose sequence has a degree of homology with the native sequence(s) (in the case of a chimeric antibody) greater than 70%, advantageously greater than 80%, preferably greater than 90% and, most preferably, greater than 95%. Such an analogue may be obtained by mutation, deletion, substitution and/or addition of one or more nucleotide(s) of the corresponding sequence(s).

In accordance with the aims pursued by the present invention, it is preferable to use an antibody directed against a tumor antigen or an epitope specific for an infectious and pathogenic microrganism, especially a virus and more particularly the HIV virus and, advantageously, an antigen strongly represented at the surface of the target cell. This type of antibody is widely described in the literature. There may be mentioned especially:

the human monoclonal antibody 2F5 (Buchacher et al., 1992, Vaccines, 92, 191–195) recognizing a continuous (ELDKWAS)(SEQ ID NO: 21) and highly conserved epitope of the transmembrane glycoprotein gp41 of the HIV-1 envelope molecule, the murine monoclonal antibody 17-1-A (Sun et al., 1987, Proc. Natl. Acad. Sci. USA, 84, 214–218) recognizing the GA733 glycoprotein present at the surface of the human colorectal carcinoma cells, an antibody directed against the protein MUG-1, and an antibody directed against the E6 or E7 protein of the HPV virus (Human Papillomavirus) especially type 16 or 18.

Within the framework of the present invention, the nucleotide sequences encoding an antibody in use within the framework of the present invention may be obtained by any conventional technique in use in the field of genetic engineering, such as PCR (Polymerase Chain Reaction), cloning and chemical synthesis. Purely as a guide, the sequences encoding the heavy and light chains of an antibody may be cloned by PCR using the degenerate oligonucleotides recognizing the conserved sequences found at the 5' and 3' ends of most immunoglobulin genes (Persson et al., 1991, Proc. Natl. Acad. Sci. USA, 88, 2432–2436; Burton et al., 1991, Proc. Natl. Acad. Sci. USA, 88, 10134–10137). The antibody function of the expression product is then checked in relation to a specific antigen as indicated above.

Another approach, which is moreover preferred, consists in using an antibody which is modified especially by a toxic substance or an immunopotentiating protein. This specific embodiment makes it possible to destroy in vivo, by a local chemotherapy (toxic substance), the target cell (cancer cell or infected cell) which carries, at its surface, the specific antigen against which the antibody part is directed or to enhance the immune reaction with respect to it (immunopotentiating substance). In the context of the toxic substance, it may be advantageous to choose antibodies which may be endocytosed by the target cell. It goes without saying that the corresponding sequences may be obtained by any conventional technique in the state of the art.

The term "toxic substance" refers to a molecule having a degradation activity drastically inhibiting cell growth or inducing cell death. This may be a molecule which is toxic by itself or indirectly, for example a protein catalyzing the synthesis of a toxic substance. These molecules may be derived from plants, animals or microorganisms. Of course, the toxic function may be fulfilled by a native toxic substance (as found in nature) or an analog thereof, which may be conventionally obtained by mutation, deletion, substitution and/or addition of one or more nucleotide(s) of the native sequence. Among the preferred toxic substances, there may be mentioned a ribonuclease, ricin, diphtheria toxin, cholera toxin, herpes simplex virus type 1 thymidine kinase (TK-HSV-1), cytosine deaminase from *Escherichia coli* or from a yeast of the genus *Saccharomyces* and the exotoxin from *Pseudomonas*. To illustrate an immunopotentiating protein (whose function is to improve the host organism's immune reaction toward the target cell), there may be mentioned the CD4 protein, the high-affinity receptor for the HIV-1 virus or an Fc receptor for IgG(FcγR). Its coupling to an antibody directed against an HIV virus antigen or a tumor antigen will make it possible, consequently, to generate a hybrid molecule having a ligand recognizing a killer cell and a ligand recognizing the target cell so as to promote its elimination more efficiently. In this context, a hybrid molecule may be used which is obtained from the fusion between an anti-HIV antibody and FcγR or between the extracellular domain of the CD4 molecule and an anti-CD3 antibody. However, these examples are not limiting and such immunopotentiating proteins are known to persons skilled in the art.

Advantageously, the toxic function is provided by a ribonuclease which may be of prokaryotic or eukaryotic origin. Among those which may be used within the framework of the present invention, there may be mentioned colicin E6, cloacin from *Escherichia coli,* nuclease from *Staphylococcus,* birnase from *Bacillus intermedius* and nuclease from *Bacillus amyloliquefaciens,* also designated by the name barnase, whose sequence is disclosed in Hartley (1988, J. Mol. Biol., 202, 913–915). However, the use of human angiogenin is most particularly preferred (Saxena et al., 1991, J. Biol. Chem., 266, 21208–21214; Saxena et al., 1992, J. Biol. Chem., 267, 21982–21986).

According to another variant, the toxic function may be exerted by TK-HSV-1. It exhibits a greater affinity, compared with the mammalian TK enzyme, for certain nucleoside analogs such as acyclovir and ganciclovir and it converts them to nucleotide precursors which are toxic for the cell. Consequently, their incorporation into the DNA of replicating cells makes it possible to kill specifically dividing cells, such as cancer cells, by a toxic effect and/or by a proximity effect ("bystander" effect).

According to another embodiment of the invention, an attenuated analog may be used which also exhibits a toxic function but to a lesser degree compared with the native toxic substance. Any mutant having an attenuated degradation activity may be used within the framework of the invention. In this context, an attenuated mutant of a ribonuclease may be used which exhibits an activity attenuated by a factor of 10 to $10^6$ or better still 10 to $10^5$ and, most preferably, $10^2$ to $10^4$ compared to the native ribonuclease from which it is derived. This variant is based on the high toxicity of the ribonucleases to cellular RNAs, which makes the molecular construction stages difficult. By way of examples, there may be mentioned the attenuated mutants of barnase K27A (Mossakowska et al., 1989, Biochemistry, 28, 3843–3850) and K27A, L89F (Natsoulis and Boeke, 1991, Nature, 352, 1632–1635). The nuclease activity may be evaluated in accordance with the method described by Shapiro et al. (1987, Proc. Natl. Acad. Sci. USA, 84, 8783–8787). Of course, it is possible to measure it by other techniques too, as indicated in Example 2.

A particularly preferred construction consists in including the nucleotide sequence encoding the said toxic or immunopotentiating substance in 5' or in 3' of the nucleotide sequence encoding all or part of an antibody. There is especially preferred the case where it is introduced downstream of the sequence encoding the heavy chain of an antibody, the said chain being deleted of the stop codon for translation and the fusion taking place in the correct reading frame. The fusion of two sequences operably constitutes a conventional molecular biology technique accessible to persons skilled in the art. Moreover, it is possible to include, at the level of the fusion, a binding sequence capable of being cleaved inside the target cell in order to release the toxin. In this context, the term "exogenous nucleotide sequence" refers to a sequence encoding all or part of an antibody optionally fused to the said substance.

Of course, the said exogenous nucleotide sequence is placed under the control of elements which are necessary for its expression. "Elements which are necessary" is understood to mean all the elements which are necessary for its transcription into messenger RNA (mRNA) and for the translation of the latter into protein. Among the elements which are necessary for the transcription, the promoter is of particular importance. In general, a promoter will be used which is functional in a eukaryotic, and especially human, cell. This may be a constitutive promoter or a regulatable promoter and it may be isolated from any gene of eukaryotic or viral origin. Moreover, a promoter in use in the present invention may be modified so as to contain regulatory sequences, such as "enhancer" type activating sequences. Alternatively, a promoter derived from immunoglobulin genes may be used when it is desired to target a lymphocytic host cell. Nevertheless, it will be preferable to use a constitutive promoter allowing expression in a large number of cell types and especially a promoter of a housekeeping gene such as the promoter of the TK-HSV-1 gene, the adenoviral promoter E1A, MLP (for Major Late promoter), the murine or human PGK (phosphoglycerate kinase) promoter, the promoter of the rat β-actin (ACT) gene, the HPRT (Hypoxantyl Phosphoribosyl Transferase) promoter, the HMG (Hydroxymethyl—Glutaryl coenzyme-A) promoter, the RSV (Rous Sarcoma Virus) promoter, the SV40 virus (Simian Virus) early promoter or the DHFR (Dihydrofolate Reductase) promoter. As a guide, when the nucleotide sequence is incorporated into a retroviral vector, the 5' LTR may be used as promoter. However, it is most particularly preferable to use an internal nonretroviral promoter, such as those specified earlier.

The exogenous nucleotide sequence may, in addition, contain other elements contributing to its expression both at the level of transcription and translation, especially an intron sequence bordered by appropriate splicing signals, a nuclear localization sequence, a sequence for initiation of translation, the elements for termination of transcription (polyadenylation signal), and/or a sequence encoding a secretory signal. The said sequence may be homologous, that is to say derived from the gene encoding the antibody in question, or heterologous, that is to say derived from any gene encoding a precursor of a secreted expression product. The choice of such elements is wide and accessible to persons skilled in the art.

For the purposes of the present invention, the exogenous nucleotide sequence provided with the elements necessary for its expression is introduced into a host cell to give a genetically modified cell. All the procedures which make it possible to introduce a nucleic acid into a cell may be used, such as for example precipitation with calcium phosphate, DEAE dextran technique, direct injection of nucleic acid into the host cell, the bombardment of gold microparticles covered with nucleic acid or the use of liposomes or of cationic lipids. However, within the framework of the present invention, the exogenous nucleotide sequence is preferably inserted into an expression vector. In particular, it may be of the plasmid type or derived from an animal virus and especially a retrovirus, an adenovirus, an adenovirus-associated virus or a herpes virus. However, the use of an integrative vector is preferred. The choice of such a vector is wide and the techniques for cloning into the vector selected are accessible to persons skilled in the art. Likewise, the process to be used to generate infectious viral particles is known.

A first vector which is particularly appropriate for the present invention is an adenoviral vector (see below).

According to another, also advantageous, alternative, a retroviral vector is used. The numerous vectors described in the literature may be used within the framework of the present invention and especially those derived from the Moloney murine leukemia virus (MoMuLV) or from the Friend's virus (FrMuLV). In general, a retroviral vector in use in the present invention is deleted of all or part of the viral genes gag, pol and/or env and comprises a 5' LTR, an encapsidation region and a 3' LTR. The exogenous nucleotide sequence is inserted preferably downstream of the encapsidation region. The propagation of such a vector requires the use of complementation lines described in the prior art, such as the lines CRE, GP+E-86, PG13, Psi Env-am-12, pA317 and psi-CRIP.

According to a preferred embodiment and as regards producing an antibody which is other than a single chain (comprising for example two heavy and light protein chains), the use of a dicistronic vector allowing the synthesis of two translational products from a single mRNA is preferred. The initiation of translation of the second translational product is preferably provided by an IRES site (for Internal Ribosome Entry Site, that is to say an internal site for entry of the ribosomes). A number of IRES sites have so far been identified and there may be mentioned that of the poliomyelitis virus (Pelletier et al., 1988, Mol. Cell. Biol., 8, 1103–1112), of EMCV (Encephalomyocarditis Virus) (Jang et al., J. Virol., 1988, 62, 2636–2643) or those described in international application WO 93/03143. But other IRES sites may also be used. This type of construction may be appropriate for any vector in use within the framework of the invention.

One of the preferred vectors within the framework of the present invention is a retroviral vector which comprises from 5' to 3':
(a) a 5' LTR derived from a retrovirus,
(b) an encapsidation region,
(c) an exogenous nucleotide sequence comprising:
   an internal promoter
   a first sequence encoding the heavy chain of an antibody,
   a ribosome entry initiation site,
   a second sequence encoding the light chain of an antibody, and
(d) a 3' LTR derived from a retrovirus.

Another preferred retroviral vector comprises an exogenous nucleotide sequence provided with the murine PGK promoter followed by a first sequence encoding the extracellular I and II domains of the CD4 molecule and a second sequence fused in phase with the first and encoding the γ3 segment of the heavy chain of the antibody 2F5 (sCD4-2F5) and, optionally, a third sequence encoding human angiogenin operably linked to the second.

It goes without saying that the order of the first, second and third sequences may be reversed. Moreover, as indicated above, the exogenous nucleotide sequence may comprise a sequence encoding a toxic or immunopotentiating substance. The latter will be preferably inserted downstream of the first sequence encoding the heavy chain of an antibody. However, the present invention is not limited to this specific embodiment.

Moreover, a vector in use within the framework of the invention may also contain other elements, for example, a gene encoding a selectable marker which makes it possible to select or identify the host cells transfected. There may be mentioned the neo gene which confers resistance to the antibiotic G418, the dhfr gene, the CAT (chloramphenicol Acetyl Transferase) gene, the puromycin acetyl transferase (pac or PURO) gene or the gpt (xanthine guanine phosphoribosyl transferase) gene.

A genetically modified cell is preferably chosen so as to be tolerated by the immune system of the host organism in which it is envisaged to graft an implant according to the invention. In this context, a nontumor and transfectable cell is most particularly preferred. They may be autologous cells removed or derived from this host organism, but also cells which are capable of being tolerated following an appropriate chemical or genetic treatment (it is for example possible to envisage repressing the expression of the surface antigens normally recognized by the host organism's immune system). It is also possible to use a syngenic cell or an allogenic cell of the same haplotype as the host organism as regards the major histocompatibility complex class II antigens.

Preferably, a genetically modified cell results from the introduction of the exogenous nucleotide sequence into autologous fibroblasts and, in particular, fibroblasts removed from the skin of a host organism. However, other cell types may be used, such as endothelial cells, myoblasts, lymphocytes and hepatocytes. Although not a preferred embodiment, it is also possible to use tumor cells (optionally attenuated by radiotherapy) removed from a host organism having tumors, in order to modify their gene pool and make them capable of inhibiting or slowing down tumor progression.

Advantageously, an implant according to the invention comprises from $10^6$ to $10^{12}$, preferably from $10^7$ to $10^{11}$, and most preferably from $10^8$ to $10^{10}$ genetically modified cells.

The present invention also relates to a method for the preparation of an implant according to the invention in which the genetically modified cells and an extracellular matrix are placed in contact. Various techniques may be used to generate an implant according to the invention. The procedure is preferably carried out in the following manner: the genetically modified cells are brought into contact with a liquid collagen solution, preferably of type I, with a biocompatible support consisting, for example, of synthetic Gore-Tex fibers coated with collagen and with at least one angiogenic growth factor, for example bFGF or VEGF (Vascular Endothelial Growth Factor). The whole is placed at 37° C. so that the collagen solution forms a gel with a dense meshwork which includes the cells and then cultured for 4 to 5 days in vitro so as to allow the genetically modified cells to colonize the implant. It is desirable to carry out the last stage of culture in a medium containing at least one angiogenic factor or a combination of two or more. In general, the techniques which make it possible to generate an implant and the culture conditions are known to persons skilled in the art.

An implant according to the invention is intended to be transplanted in a host, animal or, preferably, human organism so as to produce a therapeutic (curative and/or preventive) effect therein. Transplanted in a laboratory animal, it will make it possible, in particular, to evaluate therapeutic procedures applicable to man. The site of reimplantation is preferably the peritoneal or subcutaneous, intrarachidian or intraabdominal cavity.

The invention also extends to the therapeutic use of an implant according to the invention for the preparation of a pharmaceutical composition intended more particularly for the treatment and/or prevention of an acquired disease such as cancer or an infectious disease caused by a pathogenic microorganism (virus, parasite or bacterium). It relates especially to the treatment:

- of cancer of the uterus induced by a papillomavirus against which an implant will be used comprising autologous fibroblasts into which a sequence encoding an anti-HPV (in particular of type 16 or 18) E6 or E7 antibody has been introduced,
- of breast cancer using an anti-MUC1 antibody,
- of AIDS using an antibody directed against an envelope glycoprotein epitope conserved in numerous isolates,
- of hepatitis using an antibody directed against an epitope of the hepatitis B or C virus.

Of course, these antibodies may be modified by fusion especially to angiogenin, barnase or TK-HSV-1.

The invention also relates to a method for the treatment or prevention of acquired diseases according to which an implant according to the invention is generated in vitro and it is transplanted into a patient requiring such a treatment. The sites of reimplantation may be varied as mentioned above. Once the desired therapeutic effect is obtained, the implant simply has to be surgically removed from the patient.

Naturally, the modalities of the therapeutic procedure have to be developed by the clinician according to the patient and the disease to be treated. This procedure may be subject to numerous variants such as the number of implants according to the invention to be transplanted, the site of implantation and the type of antibody secreted as well as the level of expression. Purely as a guide, a level of expression in the patient's serum of at least 50 ng/ml of functional antibody, advantageously of at least 100 ng/ml, preferably of at least 200 ng/ml and, most preferably, of at least 500 ng/ml, is preferred. A functional antibody is an antibody capable of recognizing the antigen against which it is directed. The functionality may be determined for example by ELISA or FACS. On the other hand, when an antibody fused to TK-HSV-1 is used, it is desirable to include in the therapeutic procedure the administration of acyclovir or of ganciclovir so that its toxic effect may be exerted.

Moreover, the present invention also relates to a recombinant adenoviral vector comprising an exogenous nucleotide sequence encoding all or part of one or more protein(s) capable of forming a multimer in a host cell and, preferably, a dimer or a tetramer. For the purposes of the present invention, a recombinant adenoviral vector according to the invention may be used alone to combat an infection induced by a pathogenic organism or the establishment/propagation of a tumor in an organism or a host cell. According to a completely preferred embodiment, a recombinant adenoviral vector according to the invention comprises an exogenous nucleotide sequence as defined above (intended to express an antibody or one of its derivatives such as a fragment, a modified, chimeric antibody and the like).

A recombinant adenoviral vector according to the invention is preferably derived from a human adenovirus serotype C and, more particularly, type 2, 5 or 7. However, there may also be used other adenoviruses, especially of animal (canine, bovine, murine, avian, ovine, porcine or simian) origin or a hybrid between a variety of species. There may be mentioned more particularly the canine adenovirus CAV-1 or CAV-2, the avian adenovirus DAV or the bovine adenovirus Bad type 3 (Zakharchuk et al., 1993, Arch. Virol., 128, 171–176; Spibey and Cavanagh, 1989, J. Gen. Virol., 70, 165–172; Jouvenne et al., 1987, Gene, 60, 21–28; Mittal et al., 1995, J. Gen. Virol., 76, 93–102). The general technology relating to adenoviruses is disclosed in Graham and Prevec (1991, Methods in Mol. Biol., Vol. 7, Gene Transfer and Expression Protocols, Ed: Murray, The Human Press Inc., p109–118).

An advantageous embodiment of the present invention consists in using a vector which is defective for one or more viral function(s) which is (are) essential for replication, because of the deletion or non-functionality of one or more viral genes encoding the said function. Such a vector, which is incapable of autonomous replication, will be propagated in a complementation cell capable of providing en trans the early and/or late proteins which it cannot itself produce and which are necessary for the constitution of an infectious viral particle. The latter term designates a viral particle having the capacity to infect a host cell and to cause the viral genome to penetrate therein. By way of illustration, to propagate an adenoviral vector which is defective for the E1 function, there will be used a complementation cell such as the line 293 capable of providing en trans all the proteins encoded by the E1 region (Graham et al., 1977, J. Gen. Virol. 36, 59–72). Of course, a vector according to the invention may comprise additional deletions, especially in the nonessential E3 region so as to increase the cloning capacities, but also in the essential E2, E4, L1–L5 regions (see international application WO 94/28152). The defective functions may be complemented with the aid of a cell line or a helper virus.

A preferred adenoviral vector according to the invention is deleted of most of the E1 and E3 regions and carries, in place of the E1 region, an expression cassette comprising:

(a) a promoter, the intron of the human β-globin (BGL) gene, the sequences encoding the light chain of 2F5, the IRES site of the EMCV virus and the heavy chain of 2F5 and then the polyadenylation site of the human β-globin gene, or (b) a promoter, the intron of the human β-globin gene, the sequences encoding the molecule sCD4-2F5 optionally fused at the C-terminus and in the same reading frame to human angiogenin.

Among the promoters which may be envisaged within the framework of the present invention, there may be mentioned the adenoviral early promoter E1A, the late promoter MLP (Major Late Promoter), the murine or human PGK (Phosphoglycerate Kinase) promoter, the SV40 virus early promoter, the RSV (Rous Sarcoma Virus) virus promoter, a promoter which is specifically active in tumor cells and finally a promoter which is specifically active in the infected cells.

The invention also relates to an infectious adenoviral particle as well as to a eukaryotic host cell comprising a recombinant adenoviral vector according to the invention. The said host cell is advantageously a mammalian cell and, preferably, a human cell and may comprise the said vector in a form integrated in the genome or nonintegrated (episome). This may be a primary or tumor cell of hematopoietic origin (totipotent stem cell, leukocyte, lymphocyte, monocyte or macrophage and the like), or of muscle, hepatic, epithelial or fibroblast origin.

An infectious viral particle according to the invention may be prepared according to any conventional technique in the state of the art (Graham and Prevect, 1991, supra), for example, by cotransfection of a vector and of an adenoviral fragment into an appropriate cell or by means of a helper virus providing en trans the non-functional viral functions. It is also possible to envisage generating the viral vector in vitro in Escherichia coli (E. coli) by ligation or homologous recombination (see for example French Application 94 14470).

The subject of the invention is also a pharmaceutical composition comprising, as therapeutic or prophylactic agent, an adenoviral vector, an infectious viral particle or a eukaryotic host cell according to the invention in combination with a pharmaceutically acceptable carrier. The composition according to the invention is in particular intended for the preventive or curative treatment of acquired diseases such as cancers, viral diseases such as AIDS, hepatitis B or C or recurrent viral infections caused by the herpes virus.

A pharmaceutical composition according to the invention may be produced in a conventional manner. In particular, a therapeutically effective quantity of a therapeutic or prophylactic agent is combined with a carrier such as a diluent. A composition according to the invention may be administered locally or systemically or by aerosol. Especially preferred is the intramuscular, intratumor and intrapulmonary administration and, most particularly, intravenous injection. The administration may take place in a single dose or in a dose which is repeated once or several times after a certain interval of time. The appropriate route of administration and dosage vary according to various parameters, for example, the individual or the disease to be treated or the gene(s) of interest to be transferred. In particular, the viral particles according to the invention may be formulated in the form of doses of between $10^4$ and $10^{14}$ pfu (plaque forming units), advantageously $10^5$ and $10^{13}$ pfu and, preferably, $10^6$ and $10^{11}$ pfu. The formulation may also include an adjuvant or an excipient which is acceptable from a pharmaceutical point of view.

Finally, the present invention relates to the therapeutic or prophylactic use of an adenoviral vector, an infectious viral particle or a eukaryotic host cell according to the invention for the preparation of a medicament intended for the treatment of the human or animal body and, preferably, by gene therapy. According to a first possibility, the medicament may be administered directly in vivo (for example by intravenous injection, into an accessible tumor, into the lungs by aerosol and the like). The ex vivo approach may also be adopted which consists in removing cells from the patient (bone marrow stem cells, peripheral blood lymphocytes, muscle cells and the like), in infecting them in vitro according to prior art techniques and in readministering them to the patient.

The invention also relates to a method for the treatment or prevention of acquired diseases according to which a therapeutically effective quantity of a recombinant adenoviral vector, an infectious adenoviral particle or a host cell according to the invention is administered to a patient requiring such a treatment.

The invention is illustrated, without however being limited, by the following examples and with reference to the following figures.

EXAMPLES

Figure 1:
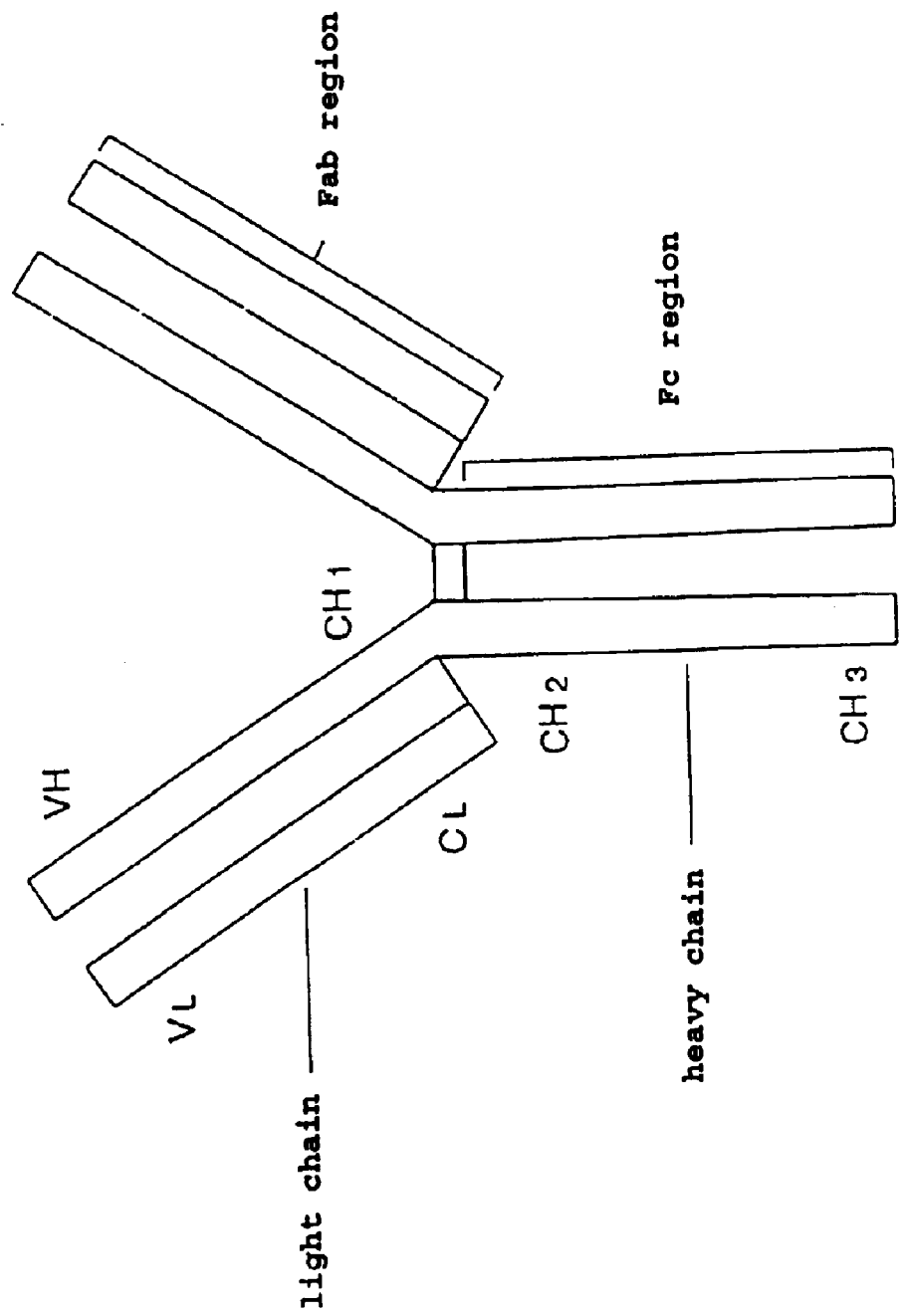
FIG. 1 is a schematic representation of the structure of an antibody and of the F(ab) and Fc fragments.

The constructions described below are carried out according to the general genetic engineering and molecular cloning techniques detailed in Maniatis et al. (1989, Laboratory Manual, Cold Spring Harbor Laboratory Press, Cold Spring Harbor, N.Y.) or according to the recommendations of the manufacturer when a commercial kit is used. As regards the repair of the restriction sites, the filling of the protruding 5' ends may be performed with the aid of the Klenow fragment of DNA polymerase of Escherichia coli (E. Coli) and the destruction of the protruding 3' ends in the presence of the T4 phage DNA polymerase or by treatment with S1 nuclease followed by repair with Klenow. The PCR techniques are known to persons skilled in the art and are abundantly described in PCR Protocols, a guide to methods and applications (Ed: Innis, Gelfand, Sninsky and White, Academic Press, Inc.).

The cloning steps using bacterial plasmids are preferably carried out by passage on the E. coli XL1-Blue strain (Stratagene), and those relating to the vectors derived from the M13 phage in E. coli NM522. The mutageneses are performed using synthetic oligodeoxynucleotides with the aid of a kit of commercial origin (for example Amersham, RPN1523) and according to the recommendations of the manufacturer.

Example 1

Preparation of an Implant Secreting the Antibody 2F5 and Intended for an Anti-AIDS Immunotherapy A. Construction of a Dicistronic Retroviral Vector for the Expression and Secretion of Anti-HIV Antibody 2F5.

The vector which forms the basis of the constructions is pLXSP which is derived from pLXSN (Miller and Rosman, 1989, BioTechniques, 7, 980–988). The latter is a retroviral vector which comprises the 5' LTR of MoMuSV (Moloney Murine Sarcoma Virus), a retroviral encapsidation region, multiple restriction sites, the neo gene for resistance to neomycin under the control of the SV40 promoter and the MoMuLV 3' LTR. The vector pLXSP is obtained after, on the one hand, the replacement of the NheI-KpnI fragment of the 3' LTR of pLXSN by an analogous fragment obtained from the MPSV (Myelo Proliferative Sarcoma Virus) 3' LTR isolated from the vector pMPSV.H-2K.IL-2R (Takeda et al., 1988, Growth Factors, 1, 59–66) and, on the other hand, introduction of the puromycin resistance gene as replacement for the neo gene. The puromycin gene is obtained from pBabe Puro described in Morgenstern and Land (1990, Nucleic Acids Res., 18, 3587–3596).

The vector pLXSP is digested with EcoRI and HpaI and an EcoRI-PstI fragment (after repairing the PstI site) isolated from pKJ-1 (Adra et al., 1987, Gene, 60, 65–74) is introduced therein. This fragment carries the promoter of the mouse PGK gene. After ligation, the vector pTG2663 is obtained. This is subjected to a digestion with the enzymes ClaI and BamHI in order to eliminate the cassette for expression of the puromycin gene. After treatment with Klenow and ligation, the vector pTG2673 is obtained in which the BamHI site is reconstituted.

The vector pTG2676 is obtained by cloning the HindIII-EcoRI fragment comprising the cDNA encoding the light chain (LC) of the monoclonal antibody 2F5 into the plasmid Bluescript SK+ (Stratagene). It may be cloned by PCR with a cDNA library derived from the mRNA of the hybridoma 2F5 (Buchacher et al., 1994, AIDS Research and Human Retroviruses, 10, 359–369; Katinger, 1992, Seventh Cent Gardes Conference, 299–303) using appropriate primers complementary to the sequences surrounding the codon for initiation of translation and the stop codon, such as the primers OTG5168 and OTG5169 (SEQ ID NO: 1 and 2). There is isolated from pTG2676 an XhoI-BamHI fragment carrying the cDNA LC 2F5 which is inserted into the vector pTG2673 previously digested with the same enzymes in order to generate pTG4336.

Figure 2:
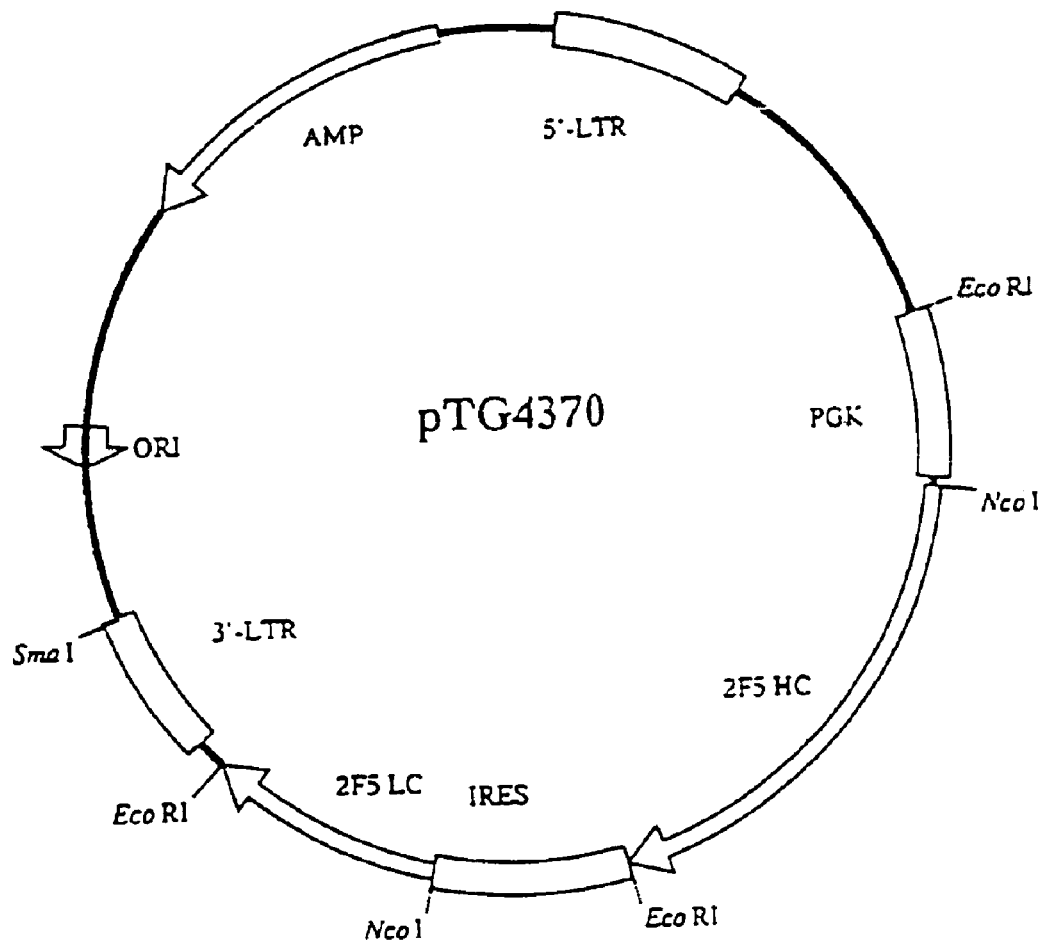
FIG. 2 is a schematic representation of the vector pTG4370 allowing the expression of the antibody 2F5.

The latter is linearized with the NcoI enzyme and subjected to ligation with, on the one hand, the NcoI-EcoRI fragment obtained from pTG2677 and carrying the cDNA encoding the heavy chain (HC) of the antibody 2F5 and, on the other hand, the EcoRI-NcoI fragment purified from pTG4369 and carrying the EMCV IRES site. The vector pTG2677 is a pBluescript SK+ in which the CDNA HC 2F5 carrying the same ends has been introduced between the HindIII and EcoRI sites. It was obtained by PCR on the preceding library with the aid of the primers OTG5170 and OTG5171 (SEQ ID NO: 3 and 4). As for the vector pTG4369, it is obtained from the cloning, also into pBluescript SK+, of the XbaI-ClaI fragment corresponding to the EMCV IRES (Jang et al., 1988, supra). The triple ligation generates the vector pTG4370 (FIG. 2). The cassette for expression of the puromycin gene may be optionally reintroduced into the plasmid part of pTG4370 so as to facilitate the selection stages. pTG6368 is obtained.

Infectious viral particles are generated in the following manner:

The ecotropic complementation line GP+E-86 (Markowitz et al., 1988, J. Virol., 62, 1120–1124) and the target cells NIH3T3 (mouse fibroblast cells), available from ATCC, are cultured at 37° C. in the presence of 5% $CO_2$ in DMEM medium (Dulbecco's Modified Eagle's Medium) containing 10% foetal calf serum (FCS) (GibcoBRL), 1 mM Glutamine, 1% nonessential amino acids and 40 µg/l of gentamicin (complete DMEM medium) The day before the transfection, the GP+E-86 cells are cultured in an amount of $5 \times 10^5$ cells per 10 cm dish. The next day, 20 µg of linearized plasmid pTG4370 and 1 µg of selection vector (for example the vector pLXSP carrying the puromycin resistance gene) are transfected according to the traditional calcium phosphate method. The following day (D+1), the cells are washed according to the prior art methods and placed in a new medium for 48 hours, before being cultured from D+3 in selective medium (5 µg/ml of puromycin).

At the end of about 2 weeks of selection, cell clones resistant to the antibiotic are visible on the dish. They are isolated according to prior art techniques and the cells resuspended in selective medium in 96-well culture plates. The clones which are the best producers of antibodies are selected using the ELISA method described below and the supernatants are titrated on NIH3T3 cells. To do this, on the day before the infection, they are inoculated at $10^5$ cells per well. The viral infections are performed according to the conventional procedure described in the literature. The titration method is the so-called limiting point method. The ELISA method makes it possible to titrate the quantity of functional 2F5 antibodies recognizing the target epitope (ELDKWAS) (SEQ ID NO: 21). The latter is chemically synthesized.

Briefly, a peptide solution (2 mg/ml) is diluted 2000 fold in a buffer (15 mM $Na_2CO_3$, 35 mM $NaHCO_3$, pH 9.6) and 100 µl are deposited at the bottom of each well of a microtiter plate and incubated at 4° C. for 16 h. After extensive washes in a PBS buffer, 0.05% Tween-20, the wells are saturated with 50 µl of 1% BSA dissolved in a PBS buffer 1 h at 37° C. After washing, 100 µl of the sample to be tested or of a standard solution are added. The plate is incubated for 2 h at room temperature and washed thoroughly with the PBS buffer-Tween 20. 100 µl of a peroxidase-conjugated anti-human IgG goat antibody are then added (concentration 0.8 mg/ml; Jackson Immuno Research Laboratories Inc, PA) diluted 1000 fold in PBS buffer, 1% BSA. After 2 hours at room temperature and extensive washes, the peroxidase enzymatic activity is revealed by addition of 100 µl of the following preparation (0.066 M $Na_2HPO_4$, 0.035 M $C_6H_8O_7$ pH5, 0.04% orthophenylenediamine and 0.014% hydrogen peroxide). The reaction is stopped by 150 µl of 1 M $H_2SO_4$. The absorbance is measured at 490 nm.

The standard solution is obtained either from a commercial source (Virus Testing Systems, Houston) or from a hybridoma supernatant concentrated on Centricon. The antibody solution (1 µg/ml) is 2-fold serially diluted in fetal calf serum. The absorbance is measured for each of the dilutions and the calibration curve is plotted (ng of antibody as a function of the absorbance). The most productive clones are thus determined.

B. Preparation of the Implant

1/Removal and Culture of Primary Fibroblasts.

Skin biopsies are performed on young 2- to 3-day old BALB/C female mice. However, other mouse lines may also be suitable. After a rough mechanical dissociation, the sample is placed in 30 ml of complete DMEM medium in the presence of 5000 units of dispase (Collaborative Medical Products) and of 1% collagenase (Sigma). After 2 hours at 37° C., the mixture is diluted and the cells are harvested by centrifugation, carefully washed before being resuspended in RPMI 1640 medium (Gibco BRL). After about one week of culture, the primary fibroblasts are infected with the culture supernatants of the producing clones selected as in the preceding stage (A) according to the conventional procedure. Fibroblast cells NIH3T3 may also be reimplanted by way of a model. They are cultured as indicated above and infected conventionally. The presence of the 2F5 antibody in the supernatants of NIH3T3 cells infected with one of the producing clones was monitored by the ELISA test and was evaluated at 500 ng/ml/24 h, that is to say a productivity of more than 1 μg/$10^6$ cells/24 h.

2/Preparation of a Neo-Organ

The PTFE fibers previously autoclaved (Gore Inc, AZ) are first of all placed in contact with a rat tail collagen solution (solution at 0.5 mg/ml in 0.1 N acetic acid) for 2 hours under vacuum. They are then spread at the bottom of a well (12-well plate), UV-sterilized, rehydrated with PBS buffer overnight before being treated for 2 hours at room temperature with angiogenic factors (10 ml of PBS containing 2 μg of bFGF and 1 μg of VEGF per 100 mg of fibers approximately).

In parallel, the infected fibroblasts (primary fibroblasts or NIH3T3) are briefly trypsinized. 1.5×$10^7$ cells are resuspended in 0.2 ml of medium and then 2 ml of the following mixture are added per well: 200 μl of 10×RPMI, 24 μl of 7.5% sodium bicarbonate, 5 μl of 1 M Hepes, 20 μl of Gentamicin, 20 μl of Glutamine, 2 μl of bFGF (10 ng/μl), 2 μl of EGF (Epidermal Growth Factor) (10 ng/μl), 1.5 ml of collagen (2 mg/ml), 12 μl of NaOH (10 N) and 15 μl of $H_2O$. After 30 to 60 minutes of incubation at 37° C., a polymerization of the mixture is observed. The latter is cultured at 37° C. for about 4 days in the presence, for the last night, of angiogenic factors (bFGF and VEGF).

C. Reimplantation of the Implant

One or two implants are introduced into the peritoneal cavity either of BALB/c female mice or of nude Swiss mice. One month after their implantation, it is checked that they have anchored to the adipose tissue of the abdominal cavity and are vascularized. Moreover, blood samples are collected regularly during the month following the implantation and the assay of the 2F5 antibody by ELISA (according to the technique described above) reveals values of the order of 20 ng/ml of serum in syngenic BALB/c mice and exceeding 100 ng/ml of serum in the nude mice. The antibody level is maintained over a period of more than 6 to 7 weeks after the implantation.

The efficacy of the 2F5 antibody to inhibit the HIV viral infection is evaluated on SCID (Severe Combined Immuno Deficiency) mice. They are immunodeficient mice possessing no T cells or mature B cells which, moreover, may be humanized by introduction of human cells or tissues. This treatment makes them infectable by HIV (Namikawa et al., 1988, Science 242, 1684–1686)

One to two neo-organs secreting the 2F5 antibody are implanted in the abdominal cavity of humanized SCID mice by intraperitoneal injection of human lymphocyte cells CEM A3 (40×$10^6$ cells). 3 to 5 weeks after the transplant, the mice are challenged with the HIV virus (1000 $TCID_{50}$ of HIV1 Bru isolate intravenously). The cells are recovered from the animal 3 days post-infection and cultured. The cell supernatant is collected at regular time intervals and the reverse transcriptase activity determined. It is observed that the human cells are protected against infection by HIV and that the protection is maintained for the entire duration of the experiment (50 days). Indeed, the reverse transcriptase activity is below the detection threshold in mice which have received a transplant of the implant secreting the 2F5 antibody (behavior similar to the noninfected control). These data reflect an inhibition of the replication of HIV in the animals producing 2F5 in their bloodstream.

Example 2

Preparation of an Implant for an Anticancer Immunotherapy

A. Construction of the Dicistronic Retroviral Vector for the Expression and Secretion of the 17-1-A Antibody In the first place, the plasmid pBluescript SK+ is digested with NotI and then subjected to a treatment with the large Klenow fragment of DNA polymerase before being self-religated. The vector pTG6336 is generated in which the NotI site has been destroyed. In parallel, the cDNA encoding the light chain of the 17-1-A antibody is isolated by PCR from a cDNA library constructed from MRNA isolated from 17-1-A hybridoma cells (Sun et al., 1987, Proc. Natl. Acad. Sci. USA, 84, 214–218; Herlyn et al., 1979, Proc. Natl. Acad. Sci. USA 76, 1438–1442). As a guide, this antibody is directed against an epitope of the transmembrane glycoprotein GA733-2 (Szala et al., 1990, Proc. Natl. Acad. Sci. USA, 87, 3542–3546) present at the surface of human colorectal carcinoma cells. The PCR uses the primers OTG6114 and OTG6115 (SEQ ID NO: 5 and 6) designed so as to introduce restriction sites facilitating subsequent cloning steps, the EcoRI and NcoI sites in 5' and the BglII and XbaI sites in 3' respectively. After checking on agarose gel, the PCR fragment thus generated is digested with EcoRI and XbaI and then cloned into pTG6336 between the same sites. pTG6339 is generated.

The latter is digested with EcoRI and NcoI and ligated to the EcoRI-NcoI fragment of pTG4369 carrying the IRES site, to give pTG6343. There is introduced into the latter the cDNA encoding the heavy 17-1-A antibody chain lacking the stop codon in the place of which there is inserted a small spacer encoding the residues Gly-Gly-Gly-Gly-Ser (SEQ ID NO: 22). The cDNA HC 17-1-A is obtained by PCR from the preceding cDNA library and using the oligonucleotides OTG6192 and OTG6194 (SEQ ID NO: 7 and 8). The insertion of the PCR fragment digested with SalI-EcoRI makes it possible to generate pTG6346.

The latter is linearized with NotI and then ligated to the NotI fragment carrying the sequence encoding barnase to give pTG6347. The gene encoding barnase is obtained by PCR from a preparation of *Bacillus amyloliquefaciens* genomic DNA and the primers OTG5147 and OTG5148 (SEQ ID NO: 9 and 10). The oligonucleotides were designed so as to introduce an NotI restriction site in 5' of the codon corresponding to the first amino acid of the mature barnase and in 3' of the stop codon. It is checked that the sequence of the PCR fragment thus generated is in conformity with that published in Hartley (1988, J. Mol. Biol., 202, 913–915).

In parallel, the NotI fragment is inserted into an M13-type vector, for example the vector M13TG130 (Kieny et al., 1983, Gene, 26, 91–99) in which an NotI site has been previously introduced inside the cloning site by site-directed mutagenesis. The modification of the restriction sites by site-directed mutagenesis is a technique known to persons skilled in the art. The vector thus obtained is subjected to a site-directed mutagenesis with the aid of the oligonucleotide OTG5299 (SEQ ID NO: 11) so as to modify the lysine residue (Lys or K) at position 27 of the native barnase by an alanine residue (Ala or A). Next, the modified NotI fragment is isolated and introduced, as above, into the vector pTG6346 to give pTG6348.

Figure 3:
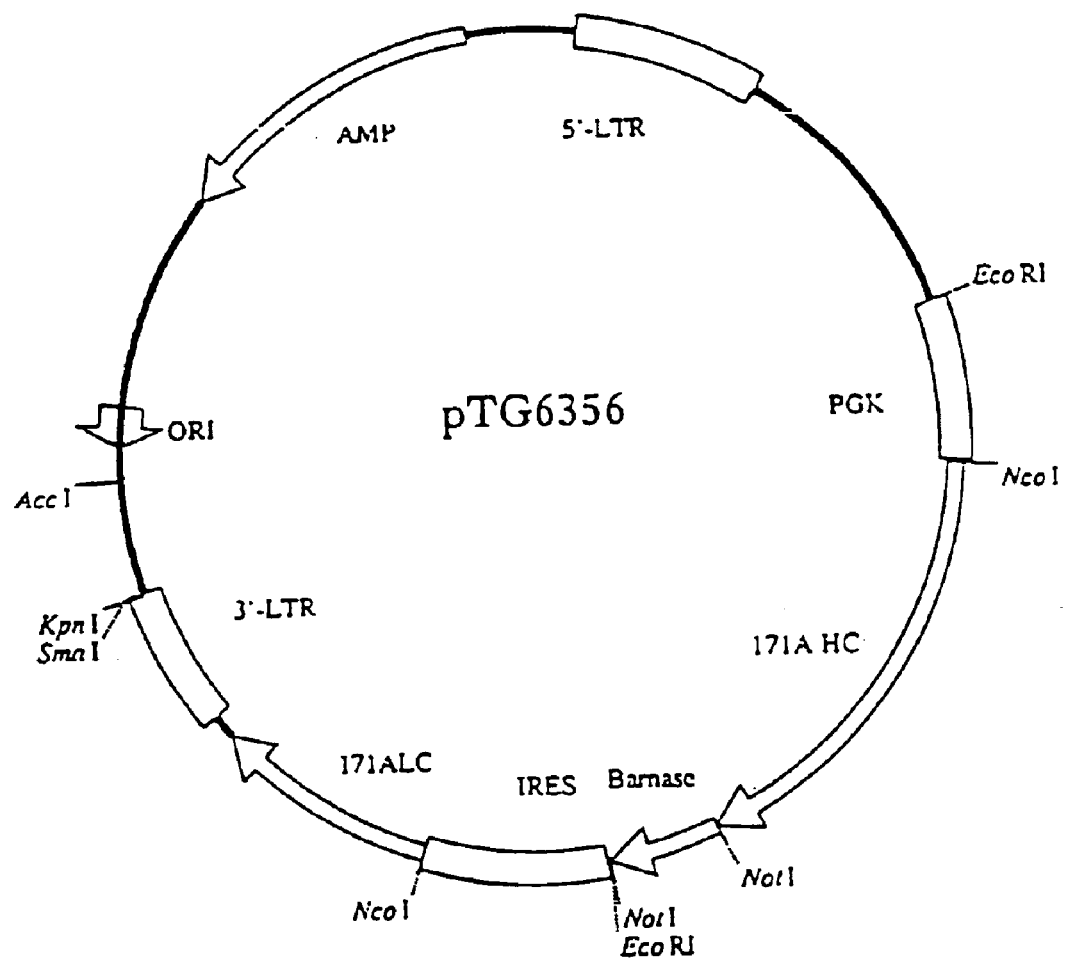
FIG. 3 is a schematic representation of the vector pTG6356 allowing the expression of the antibody 17-1-A coupled to the native barnase.
Figure 4:
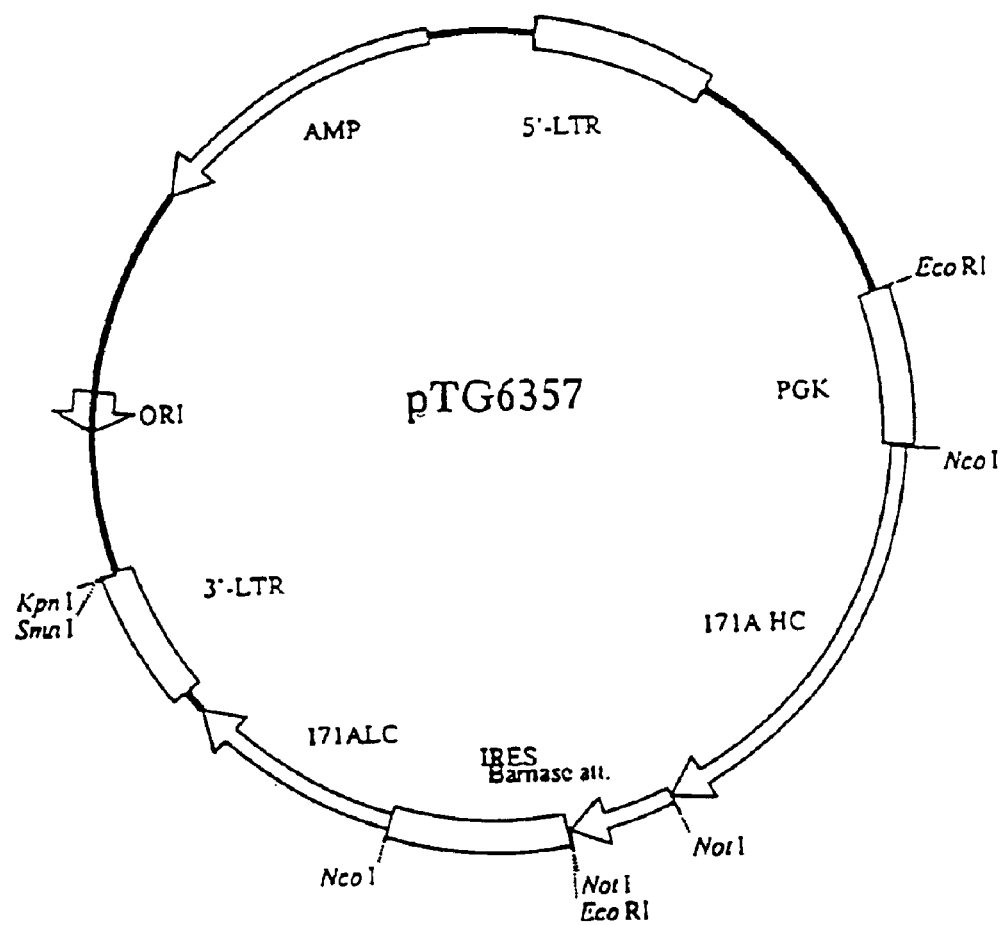
FIG. 4 is a schematic representation of the vector pTG6357 allowing the expression of the antibody 17-1-A coupled to the attenuated barnase K27A.

The SalI-BglII fragment isolated from the vector pTG6347 or pTG6348 is transferred into the vector pTG2673 previously digested with XhoI and BamHI. The vectors pTG6356 and pTG6357 are obtained respectively (FIGS. 3 and 4).

Figure 5:
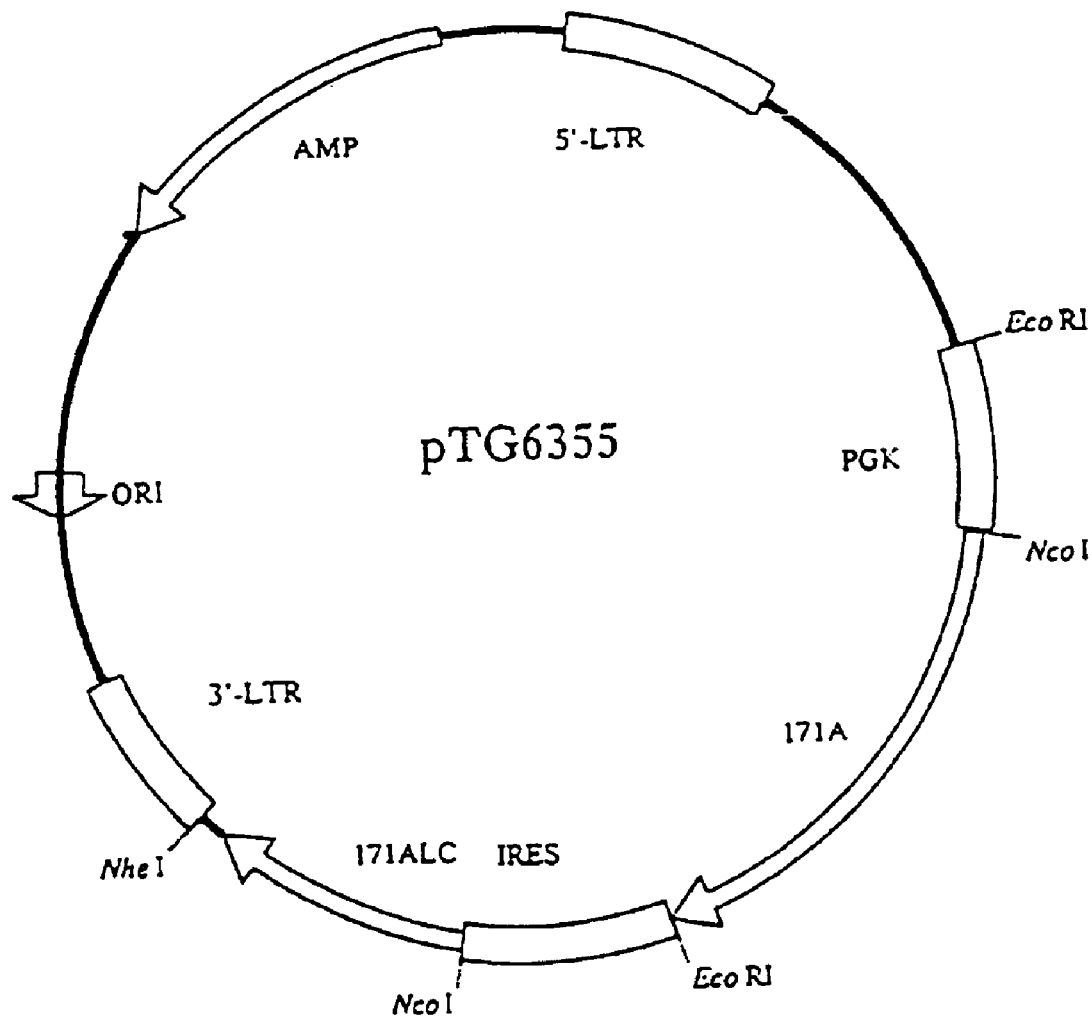
FIG. 5 is a schematic representation of the vector pTG6355 allowing the expression of the antibody 17-1-A.

Moreover, a dicistronic vector is constructed which contains the sequences encoding HC 17-1-A, the EMCV IRES followed by LC 17-1-A. The HC fragment provided with a stop codon is obtained by PCR from the vector pTG6346 with the oligonucleotides OTG6192 (SEQ ID NO: 7) and OTG6193 (SEQ ID NO: 12). This PCR fragment, which is equipped with SalI and EcoRI sites at its 5' and 3' ends respectively, is inserted into the vector pTG6343 digested with the same enzymes to give pTG6345. The SalI-BglII fragment of the latter is cloned between the XhoI and BamHI sites of pTG2673. The vector pTG6355 is obtained (FIG. 5).

Viral particles are generated by transfection of the GP+E-86 cells with the vectors pTG6355, pTG6356 and pTG6357 (cotransfection with pLXSP) according to the technique described in Example 1, the only difference being that the transfected clones are tested for the production of 17-1-A antibodies as indicated below. 100 μl of anti-murine immunoglobulin antibody (Southern Biotechnology) previously diluted 100 fold in a buffer (80 mM $Na_2CO_3$, 200 mM $NaHCO_3$, pH9.6) are distributed in the wells of a microtiter plate (Nunc) and incubated overnight at 4° C. The nonadsorbed antibodies are removed by extensive washes with 1×PBS buffer, 10 mM EDTA, 0.05% Tween 20. The wells are saturated by addition of 200 μl of a 1×PBS solution, 1% BSA (Bovine Serum Albumin) 1 h at 37° C. After this stage, the plate is again washed, and then the control series (diluted in 1×PBS, 1% BSA) or the culture supernatants to be tested are deposited and incubated for 2 h at room temperature, with agitation. After several washes, the plates are incubated with 100 μl of an anti-$Ig_2a$ goat antibody (isotype of 17-1-A), coupled to biotin (Southern Biotechnology) diluted 5000 fold in 1×PBS buffer, 1% BSA. After 1 h of incubation at room temperature with agitation, the excess is removed by 8 washes and then 100 μl of a peroxidase-streptavidin solution (Amersham), diluted 1000 fold, are distributed. After incubation for 45 min followed by extensive washes, the enzymatic activity is revealed by addition of 100 μl of substrate solution (for one plate: 12.5 ml of 25 mM citrate buffer, 50 mM $Na_2HPO_4$, pH 5; 1 pastille of 5 mg of OPD (ortho-phenoldiamine, Sigma); 5 μl of 35% $H_2O_2$). The reaction is stopped by addition of 25 μl of 3M $H_2SO_4$ per well. The absorbance is then read at 490 nm.

The quantity of antibody present in the culture supernatants is established as a function of a calibration series prepared as follows: the 17-1-A hybridoma cells are injected into "nude" mice. After formation of ascites, the ascitic fluid is collected and the 17-1-A antibody is purified therefrom by passage on a protein A sepharose column. This is a conventional technique accessible to persons skilled in the art. A solution of purified 17-1-A antibody is prepared at a concentration of 1 μg/ml and then 2-fold serially diluted in a PBS buffer. The absorbance is measured for each of the dilutions and the calibration curve is established (ng of antibody as a function of the absorbance). The most productive clones secrete, according to the transfected vector, from 200 to 900 ng of 17-1-A antibody/$10^6$ cells/24 h.

B. Preparation of the Implant

The NIH3T3 cells are infected with the most productive clones (derived from the transfection of the GP+E-86 cells with the vectors pTG6355, pTG6356 and pTG6357) and the culture supernatants tested by ELISA for the secretion of 17-1-A antibody. An antibody level varying from 100 to 1000 ng/$10^6$ cells/24 hours is detected according to the constructs.

Moreover, it is checked that the antibody produced recognizes the GA733 antigen expressed by the SW948 cells. For that, the flow cytometry technique is used. The SW948 cells (ATCC CCL237) are cultured in complete DMEM medium. They are detached by the action of trypsin, counted and then $5\times10^5$ cells are distributed in wells of a 96-well plate. This plate is centrifuged for 1 min at 1000 rpm, without brakes, to pellet the cells. The supernatant is removed and then the plate is vortexed and the cells resuspended in 100 μl of FACS buffer (cationic 1×PBS, 1% BSA, 0.1% human γ globulins, 5 mM EDTA). The plate is again centrifuged and the supernatant removed. The cells are then resuspended in the culture supernatant to be tested or in a dilution of the control antibody in FACS buffer and incubated for 1 h at 4° C. 4 washes are then carried out under the conditions described above and then the cells are resuspended in 100 μl of a fluorescein-coupled anti-mouse immunoglobulin goat F(ab')$_2$ fragment (DTAF) (Jackson Immuno Research Laboratories) diluted 100 fold in FACS buffer. Another incubation of 1 h at 4° C. allows the antibody to bind. The excess is then removed by 4 washes and the cells are finally resuspended in 300 μl of cationic 1×PBS before being analyzed with a flow cytometer FACScan (Becton Dickinson). It is observed that all the NIH3T3 supernatants tested (resulting from the infection with 3 types of viral particles) secrete an antibody capable of binding to the target GA733 protein.

In the case of the constructs where the antibody is fused to barnase or to the attenuated version thereof (pTG6356 and pTG6357), it is advantageous to be able to check that the fused antibody has a nuclease activity. For that, the degradation of a tRNA is monitored. 100 μl of supernatants to be tested or of an RNAseA solution at a known concentration (as reaction control) are added to 200 μl of 0.5 M Tris-HCl, pH 7.5, 5 mM EDTA, 0.5 mg/mg of BSA and 1 mg/ml final of tRNA and incubated at 37° C. for 30 min. The tubes are then placed on ice and 700 μl of 6% perchloric acid are added to precipitate the tRNA for 10 min on ice. A 10 min centrifugation at a maximum speed at 4° C. makes it possible to pellet the tRNA, leaving in suspension the free nucleotides released by the action of the enzyme. The absorbance of these nucleotides is then read at 260 nm.

The implant may be constituted according to the method indicated in Example 1 by incorporation of primary murine fibroblasts or of NIH3T3 cells, transduced with the vectors pTG6355, pTG6356 or pTG6357.

Example 3

Figure 6:
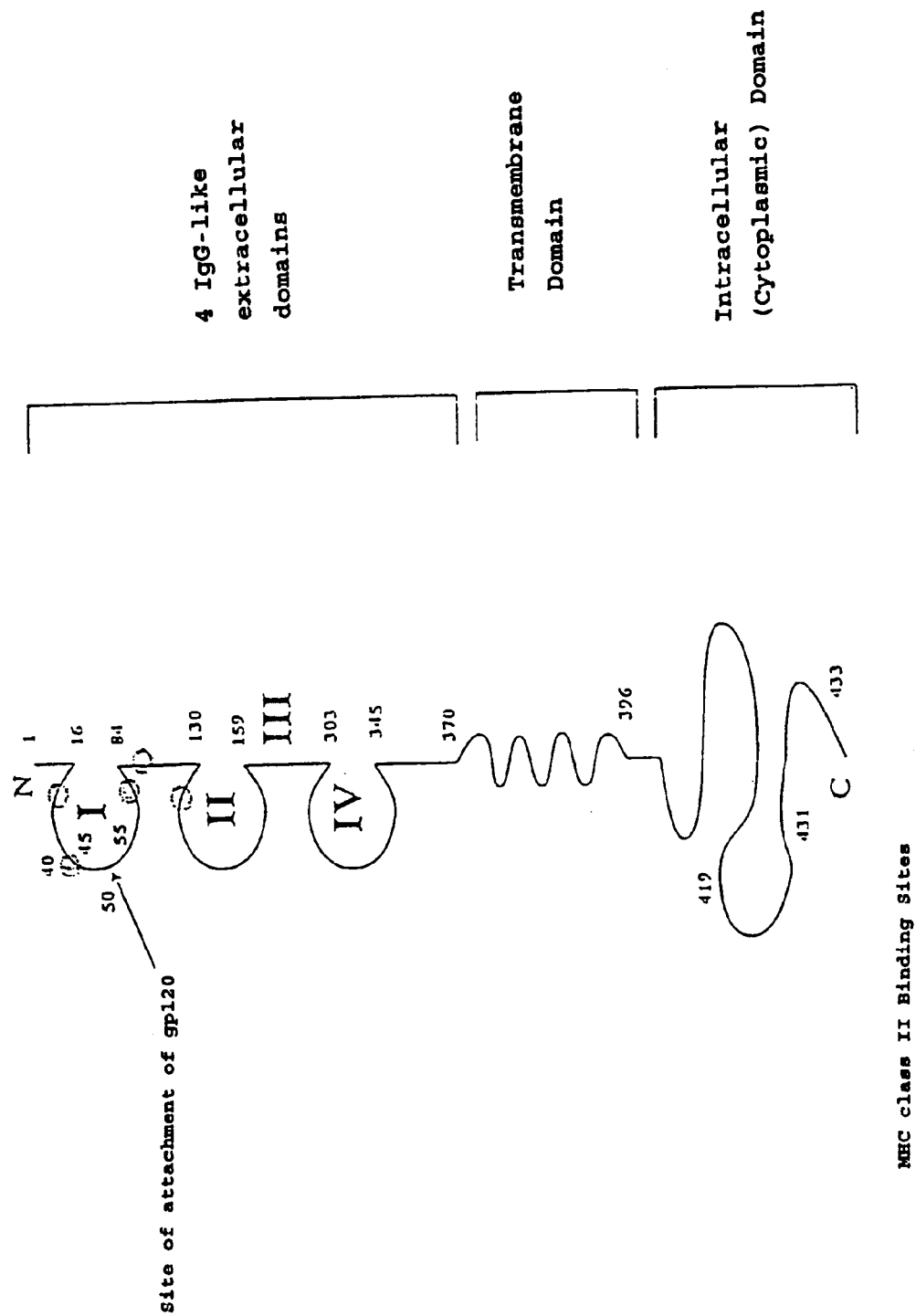
FIG. 6 is a schematic representation of the structure of the CD4 membrane protein.

Preparation of an Implant Secreting an Immunoadhesin and Intended for an Anti-AIDS Immunotherapy The aim is to produce an immunoadhesin resulting from the fusion of an "adhesive" molecule binding the HIV virus glycoprotein and of an immunoglobulin stabilizing the structure and conferring a nonspecific immunity. The adhesive part is derived from the CD4 membrane protein (structure represented in FIG. 6) from which the N-terminal part is retained (signal sequence and I and II domains of the extracellular region). Several studies have shown that they are capable, by themselves, of binding gp120, of blocking the interaction and the penetration of HIV into CD4$^+$ target cells (Traunecker et al., 1988, Nature 331, 84–86; Deen et al., 1988, Nature 331, 82–84; Hussey et al., 1988, Nature 331, 78–81; Fisher et al., 1988, Nature 331, 76–78). The immunoglobulin part consists of the constant γ3 region (hinge region —CH2—CH3) of the 2F5 antibody. The hybrid molecule is subsequently designated sCD4-2F5.

Figure 7:
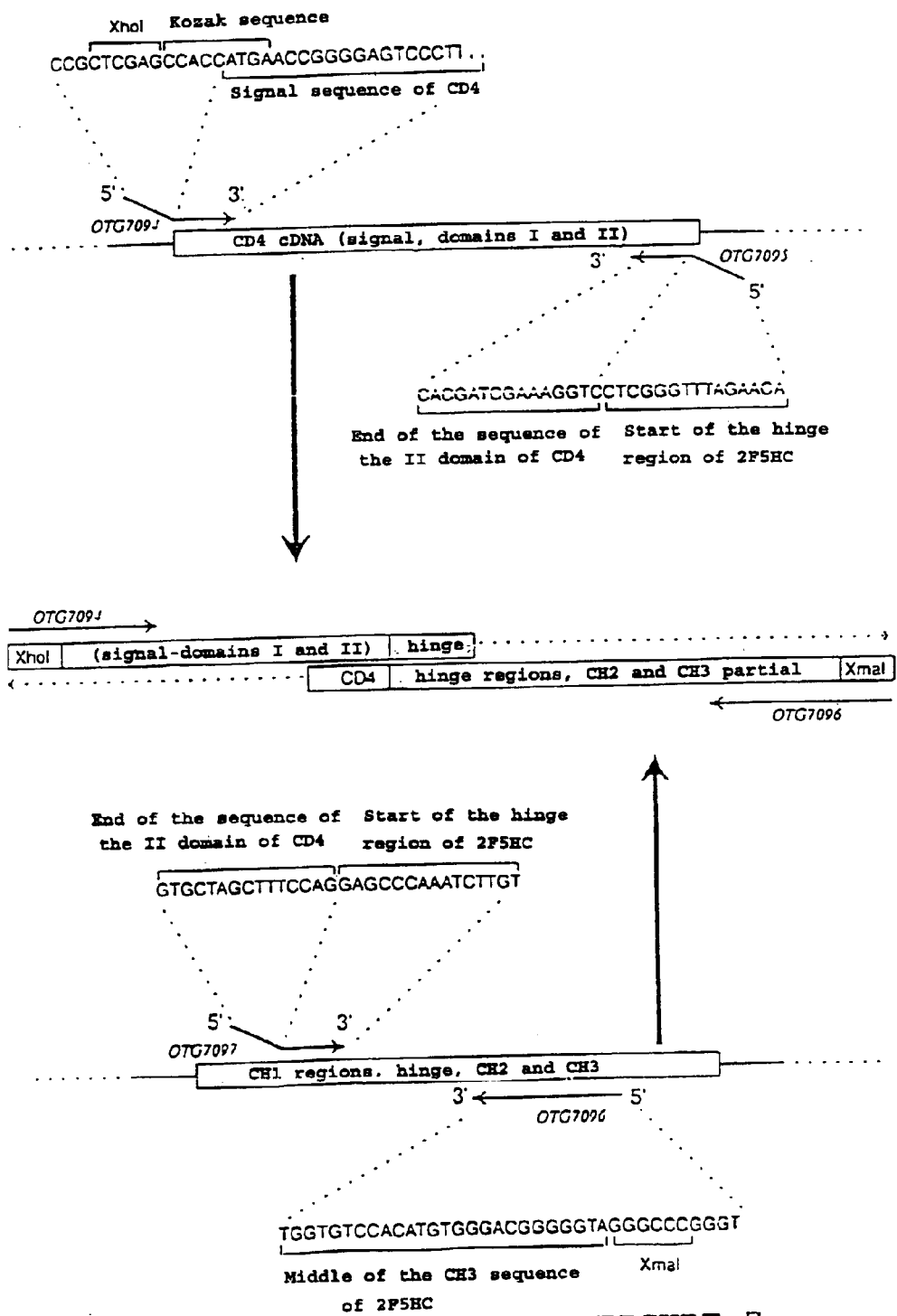
FIG. 7 is a representation of the scheme for the construction of sequences encoding the hybrid molecule sCD4-2F5 using primers OTG7094, OTG7095, OTG7096 and OTG7097 (SEQ ID NOS: 13, 14, 16 and 15).

The construction is carried out in the following manner (see FIG. 7):

The sequences encoding the sCD4 region (signal sequence—I and II domains) are conventionally isolated by PCR. As template, there is used the CDNA CD4 described in the literature (obtained from mRNA of CD4+ cells) or a prior art plasmid in which the CDNA is cloned (Jay Maddon et al., 1985, Cell 42, 93–104), which is hybridized with the primers OTG7094 and OTG7095 (SEQ ID NO: 13 and 14). The first makes it possible to introduce an XhoI site and Kozak type consensus sequences upstream of the CD4 initiator ATG and the second carries nucleotides corresponding, on the one hand, to the C-terminal end of the II CD4 domain and, on the other hand, to the N-terminal end of the hinge region of the 2F5 HC. The reaction occurs over 25 cycles (1 min at 94° C., 2 min at 50° C. and 3 min at 72° C.).

The sequences encoding the constant γ3 segment of the 2F5 HC are also amplified by PCR. The plasmid pTG2677 and the primers OTG7097 and OTG7096 (SEQ ID NO: 15 and 16) are used. The first is complementary to OTG7095 and the second covers the XmaI site situated within the CH3 region.

The PCR products thus generated overlap over 30 bp. They are rehybridized and subjected to a second amplification reaction which occurs in 2 stages, in the first instance, a linear amplification to extend the rehybridized product (10 cycles: 1 min at 94° C., 2 min at 37° C. and 3 min at 72° C.) followed by an exponential amplification in the presence of the primers OTG7094 and OTG7096 (SEQ ID NO: 13 and 16) (20 cycles: 1 min at 94° C., 2 min at 50° C. and 3 min at 72° C.).

Figure 8:
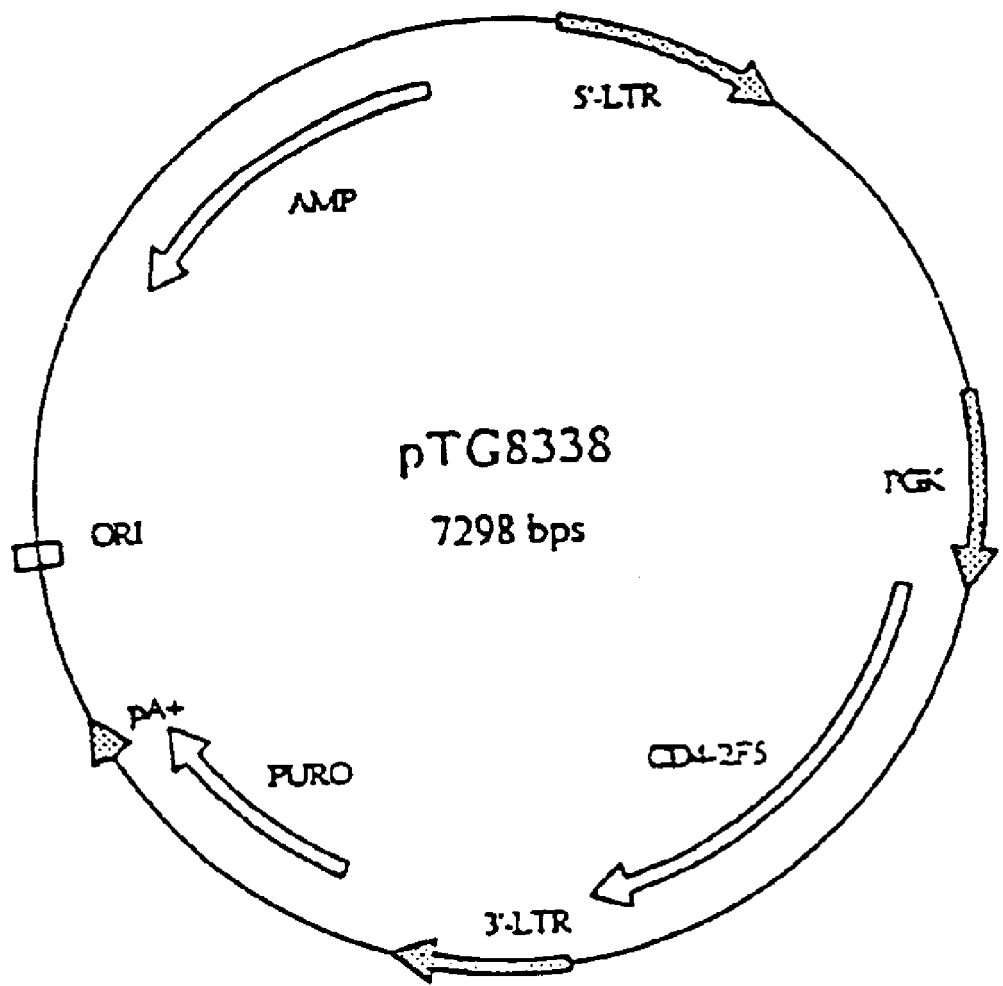
FIG. 8 is a schematic representation of the retroviral vector pTG8338 allowing the expression of the hybrid molecule sCD4-2F5.

The final product is inserted between the XhoI and XmaI sites of pTG2677 to give pTG8332 in order to reconstitute the complete sCD4-2F5 molecule. The latter is excised by XhoI-BamHI digestion and cloned downstream of the murine PGK promoter into the vector pTG6368. pTG8338 is obtained (FIG. 8).

The NIH3T3 cells are transfected with 10 μg of BglII-linearized pTG8338. Two days later, the cells are cultured in an increasing puromycin concentration (5 to 75 μg/ml). The expression of the sCD4-2F5 protein is verified by immunofluorescence using an antibody which recognizes either the CD4 part (Leu3A; Becton Dickinson) or the 2F5 part (mouse monoclonal antibody to the hinge region of a human IgG3; Interchim) and a conjugate consisting of a fluorescein-coupled anti-mouse Ig donkey antibody (Jackson Laboratories). It is noted that about 30% of the cellular pool expresses a detectable level of immunoadhesin. For this reason, producing clones are isolated by clonal dilution.

The production of the viral particles is carried out in transfected GP+E-86 cells according to the conventional procedure and selected in the presence of puromycin. The target NIH3T3 cells are then infected with the cell supernatant and the immunofluorescence analyses confirm the expression of the transgene in 100% of the cells.

The quantification is performed by ELISA. In the first place, 500 ng of HIV-1 virus gp160 envelope glycoprotein are deposited so as to bind the CD4 part of the CD4-2F5 molecule. It is produced by the recombinant route as indicated in international application WO 92/19742. The supernatant to be assayed is then added and, finally, an antibody directed against the 2F5 part (peroxidase-conjugated anti-human Ig goat antibody; Interchim). The calibration solution consists of the recombinant immunoadhesin purified from the culture supernatants on a fast-flow sepharose-G protein column (Pharmacia). A productivity greater than 10 μg/ml/24 h/$10^6$ cells is measured on the supernatants of the infected NIH 3T3 cells. This test also indicates that the protein is capable of binding gp160 and, consequently, would be capable of binding the HIV virus in order to exert its therapeutic function.

The infected NIH3T3 cells are amplified by culturing in F175 flasks. 4 organoids each containing about $10^7$ cells are generated by applying the technology detailed in Example 1 and transplanted in the peritoneal cavity of 4 nude BALB/c female mice. The secretion of immunoadhesin into the serum is monitored up to 5 weeks post implantation (assay by ELISA). The results indicate a concentration of the order of 100 to 200 μg/ml and a continuous secretion during the duration of the experiment.

Example 4

Preparation of an Implant Secreting a Protein Resulting from the Fusion of the Immunoadhesin sCD4-2F5 and of the Human Angiogenin Angiogenin is a 14.1 kDa plasma protein belonging to the family of ribonucleolytic enzymes. However, its lytic action is more limited than that of the reference ribonuclease A (RNase A) and shows a marked preference for certain RNAs (especially the 18S and 28S ribosomal RNAs and the transfer RNAs). The gene and the cDNA were cloned about ten years ago (Kurachi et al., 1985, Biochemistry 74, 5494–5499).

The fusion of the sequences encoding angiogenin downstream of sCD4-2F5 should allow the synthesis of a protein capable of targeting and destroying the cells infected with HIV. They were obtained by PCR from the plasmid pHAG1 (Kurachi et al., 1985, supra) with the aid of the primers OTG10089 and OTG10090 (SEQ ID NO: 17 and 18) comprising at their 5' ends the EcoRI and BamHI restriction sites situated in 5' of the first codon of the mature protein and in 3' of the stop codon, respectively.

For reasons of stearic hindrance, it is chosen to introduce a spacer between the two entities. The PCR reaction is carried out with the aid of the template pTG2677 and the oligonucleotides OTG10087 and OTG10088 (SEQ ID NO: 19 and 20) in order to amplify the part of the 2F5 gene stretching from the XmaI site (inside CH3) to the stop codon. The primer OTG10088 is designed to eliminate the stop codon and introduce in 3' a BamHI site as well as the spacer encoding the residues Gly-Gly-Gly-Gly-Ser (SEQ ID NO 22).

Figure 9:
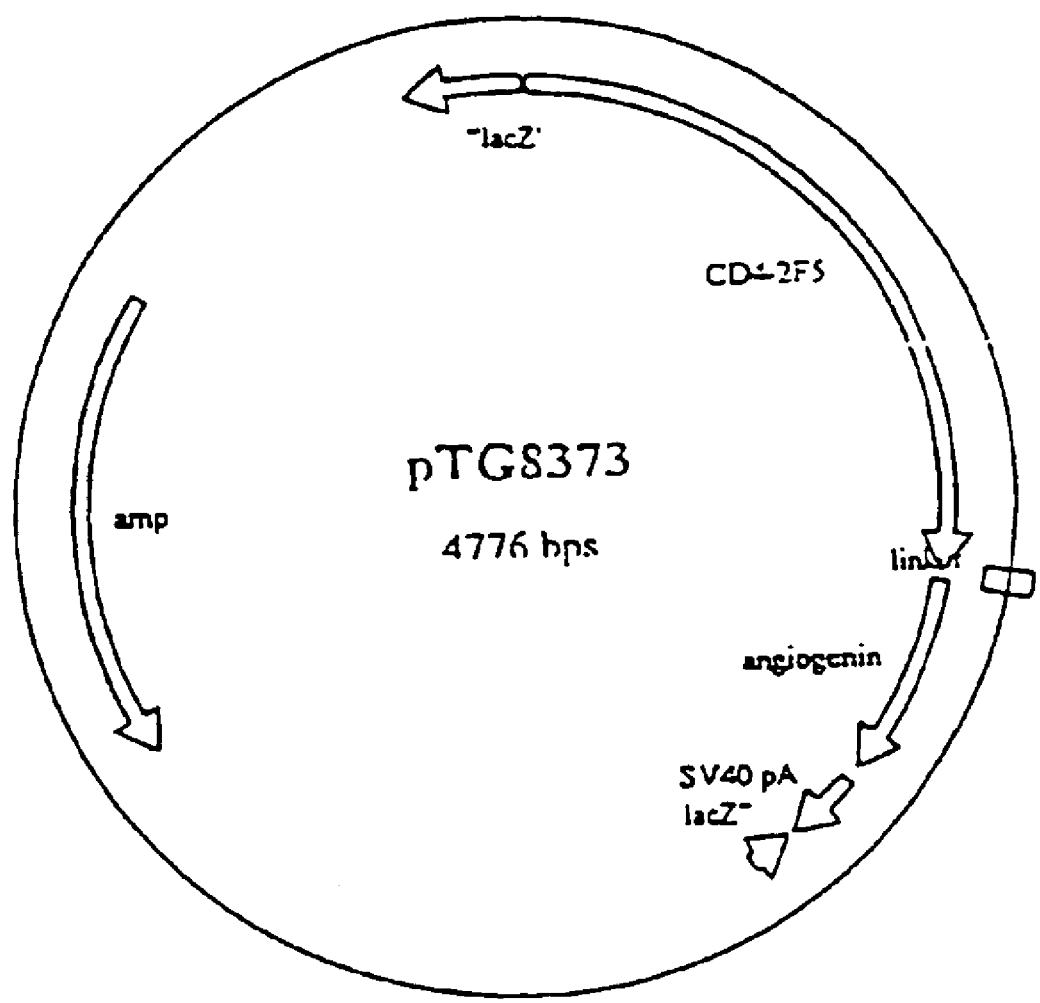
FIG. 9 is a schematic representation of the vector pTG8373 comprising the sequences encoding the fusion molecule sCD4-2F5-Angiogenin.

The two PCR fragments obtained, bordered by a BamHI site are ligated together. The XmaI-EcoRI fragment is isolated and inserted, first into pbluescript in order to verify the sequence and, finally into the vector pTG8332 in order to reconstitute the complete fusion sequence "sCD4-2F5-Angiogenin". pTG8373 is obtained (FIG. 9). The complete unit may be excised by XhoI-BglII digestion and cloned into the retroviral vector pTG6368 linearized with XhoI and BamHI. The viral particles may be constituted as above and the organoids generated from infected target cells NIH3T3 or primary fibroblasts.

Example 5

Preparation of an Adenoviral Vector Expressing the Immunoadhesin sCD4-2F5.

The adenoviral genome fragments used in the constructions described below are indicated precisely according to their position in the nucleotide sequence of the type 5 adenovirus (Ad5) genome as disclosed in the Genebank data bank under the reference M73260.

The intron and the polyadenylation signal (pA) of the β-globin human gene are obtained from the vector pBCMG/Neo (Karasuyama, 1988, Eur J. Immuno. 18, 97–104; Karasuyama, 1989, J. Exp. Med. 169, 13–25) and introduced into the plasmid pREP4 (InVitogen™) downstream of the RSV virus 3' LTR. The cassette "RSV-intron-pA β-globin promoter" is isolated from the preceding vector in the form of a SalI-BamHI fragment and inserted into the vector pTG9350. The latter is obtained from the cloning of the Ad5 genomic sequences stretching from nucleotides 1 to 458 and 3328 to 5788 in p polyII (Lathe et al., 1987, Gene 57, 193–201).

A polylinker provided with multiple cloning sites (EcoRI, XhoI, NotI, xbaI, SpeI, BamHI, EcoRV, HindIII, ClaI, KpnI and BglII) is introduced into the vector pTG8346 obtained in the preceding stage (between the intron and pA), to create pTG8347.

The sequences encoding the hybrid protein sCD4-2F5 are isolated from the vector pTG8338 (Example 3) by XhoI-BamHI digestion and introduced into the vector pTG8347 cleaved with XhoI and BglII1, to generate pTG8349 which allows their expression under the control of the RSV promoter.

Figure 10:
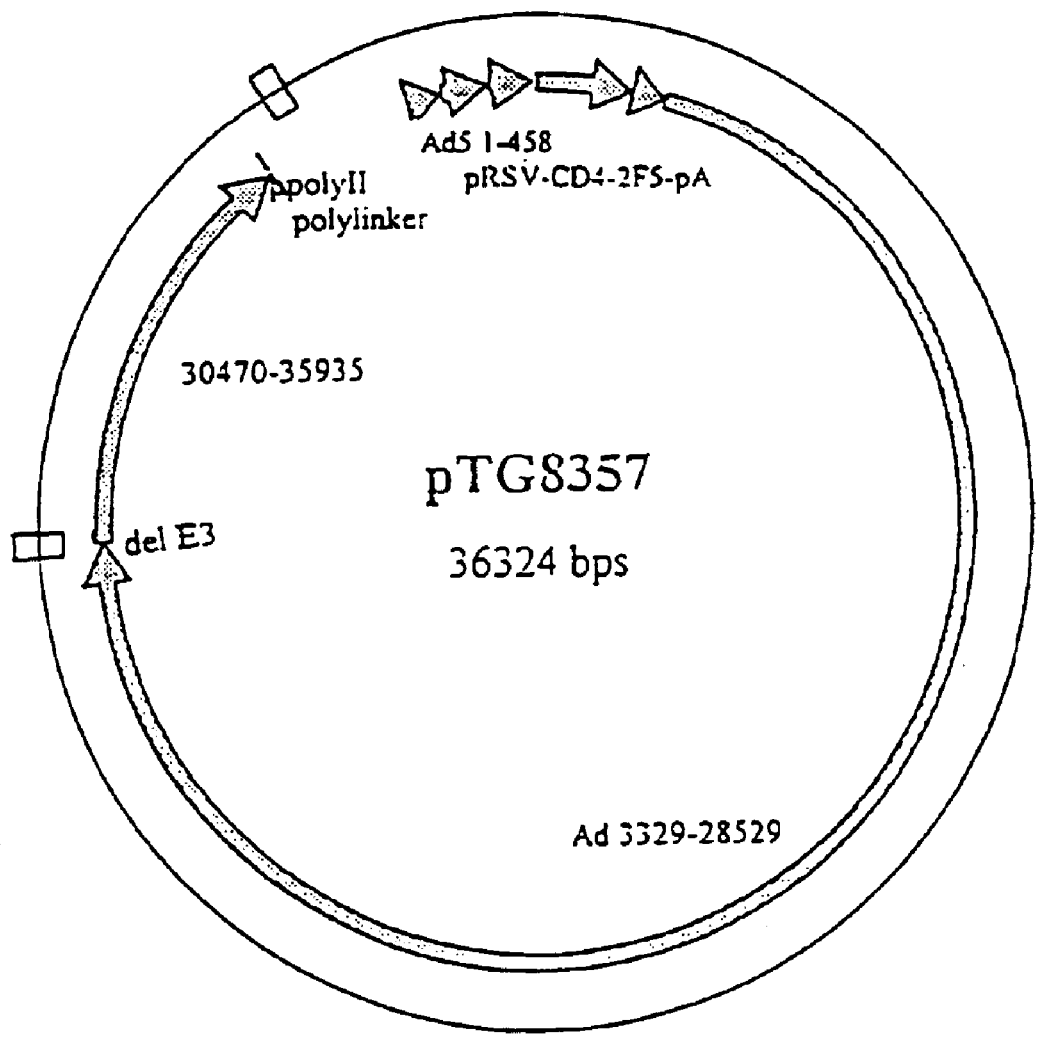
FIG. 10 is a schematic representation of the adenoviral vector pTG8357 allowing the expression of the hybrid molecule sCD4-2F5.

The in vitro homologous recombination technique (described in French Application 94 14470) is used to reconstitute the complete genome of the recombinant vector. There is used to this end the vector pTG4656 which comprises the Ad5 genome deleted of the E1 and E3 regions (Ad5 1 to 458—Ad2 MLP promoter—LacZ gene—pA SV40—Ad5 3329 to 28529 and 30470 to 35935). Any other E1⁻ E3⁻ adenoviral vector may also be suitable, such as those described in international application WO 94/28152. The BJ5183 cells (Hanahan, 1983, J. Mol. Biol. 166, 557–580) are cotransformed by pTG4656 linearized with the enzyme ClaI (10 to 20 ng) and the PacI-BstXI fragment purified from pTG8349 (about 10-fold molar excess). The recombination at the level of the homologous adenoviral sequences causes the replacement of the LacZ cassette of pTG4656 by that of sCD4-2F5 (RSV promoter—β-globin intron—sCD4-2F5 gene—pA β-globin) carried the fragment derived from pTG8349. The vector pTG8357 is generated (FIG. 10).

The recombinant viruses are obtained by transfection of pTG8357 into the cells 293 (ATCC CRL1573). 5 plaques are selected which are amplified by culturing in F25 flasks in the presence of fresh 293 cells. After 5 days, the infected cells are harvested and subjected to a HIRTH analysis (Gluzman and Van Doren, 1983, J. Virol. 45, 91–103), in order to verify the presence of the transgene. Briefly, the HIRTH analysis consists of an extraction of the adenoviral genome, a precipitation of the viral DNA, a digestion with an appropriate restriction enzyme, a transfer onto a membrane and a hybridization with a radioactive probe capable of hybridizing with the sCD4-2F5 sequences. A positive signal is observed for the 5 adenoviruses analyzed.

A substantial adenoviral stock is constituted by successive amplification in the 293 cells, purification on two cesium chloride gradients and dialyses. This stock may be used in the context of clinical anti-AIDS tests.

Example 6

Preparation of an Adenoviral Vector Expressing the Cytotoxic Immunoadhesin sCD4-2F5-Angiogenin.

Figure 11:
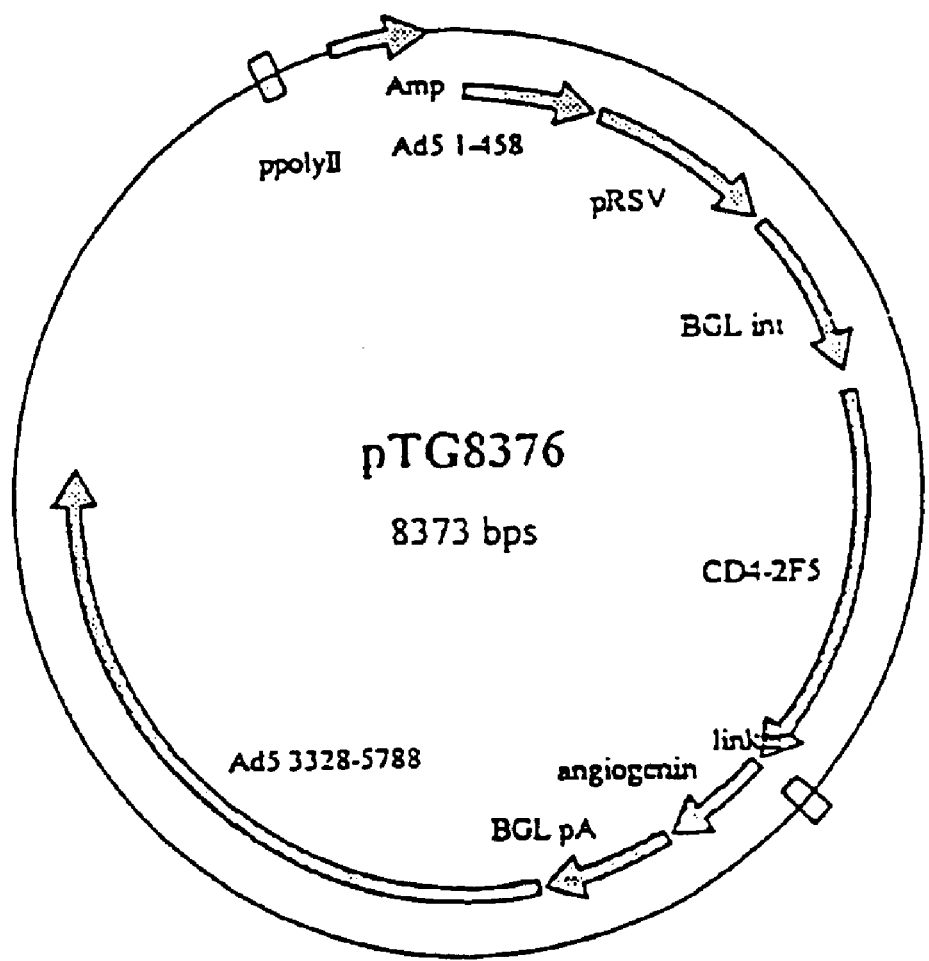
FIG. 11 is a schematic representation of the adenoviral vector pTG8376 allowing the expression of the fusion molecule sCD4-2F5-Angiogenin.

The sequences encoding the fusion protein sCD4-2F5-angiogenin are excised from the vector pTG8373 (Example 4) by XhoI-BglII digestion and cloned at the level of the same sites in the vector pTG8347 (Example 5). The vector pTG8376 is obtained (FIG. 11) which may be subjected to homologous recombination with an adenoviral vector, for example pTG4656, to produce the defective recombinant adenoviruses expressing the cytotoxic immunoadhesin directed against the cells infected with the HIV virus.

What is claimed is:

1. A recombinant adenoviral vector derived from a human adenovirus comprising an exogenous nucleotide sequence encoding all or part of an antibody, wherein said all or part of an antibody is capable of recognizing a tumor antigen or an epitope specific for an infectious and pathogenic organism, wherein said all or part of an antibody is modified at the N-terminus by fusion to extracellular domains I and II of CD4, and wherein said exogenous nucleotide sequence is under the control of elements necessary for expression of said modified antibody.

2. The recombinant adenoviral vector according to claim 1, wherein said antibody is selected from the group consisting of a native antibody, a chimeric antibody, an antibody fragment and a bispecific antibody.

3. The recombinant adenoviral vector according to claim 1, wherein it is defective for replication.

4. The recombinant adenoviral vector according to claim 3, wherein it lacks at least all or part of the E1 region and, optionally, all or part of the E3 region.

5. The recombinant adenoviral vector according to claim 1, wherein the elements necessary for the expression comprise a promoter selected from the group consisting of the adenoviral early promoter E1A, the late promoter MLP (Major Late Promoter), the murine or human PGK (Phosphoglycerate kinase) promoter, the SV40 virus early promoter, the RSV (Rous Sarcoma virus) virus promoter, and a tumor-specific promoter.

6. An infectious viral particle comprising a recombinant adenoviral vector according to claim 1.

7. A eukaryotic host cell comprising a recombinant adenoviral vector according to claim 1.

8. A pharmaceutical composition comprising a recombinant adenoviral vector according to claim 1, in association with a pharmaceutically acceptable carrier.

9. The pharmaceutical composition according to claim 8, comprising $10^4$ to $10^{14}$ pfu.

10. The pharmaceutical composition according to claim 8, wherein it is in injectable form.

* * * * *